US009694189B2

(12) United States Patent
Maile et al.

(10) Patent No.: US 9,694,189 B2
(45) Date of Patent: Jul. 4, 2017

(54) METHOD AND APPARATUS FOR COMMUNICATING BETWEEN MEDICAL DEVICES

(71) Applicant: Cardiac Pacemakers, Inc., St. Paul, MN (US)

(72) Inventors: Keith R. Maile, New Brighton, MN (US); Michael J. Kane, Roseville, MN (US); Paul Huelskamp, St. Paul, MN (US); Lance E. Juffer, Lino Lakes, MN (US); Jeffrey E. Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/812,591

(22) Filed: Jul. 29, 2015

(65) Prior Publication Data
US 2016/0038748 A1    Feb. 11, 2016

Related U.S. Application Data

(60) Provisional application No. 62/034,017, filed on Aug. 6, 2014, provisional application No. 62/033,932, filed on
(Continued)

(51) Int. Cl.
*A61N 1/37* (2006.01)
*A61N 1/372* (2006.01)
(Continued)

(52) U.S. Cl.
CPC ..... *A61N 1/37288* (2013.01); *A61N 1/37217* (2013.01); *A61N 1/3962* (2013.01);
(Continued)

(58) Field of Classification Search
USPC ........................ 607/31, 32, 59, 60
See application file for complete search history.

(56) References Cited

U.S. PATENT DOCUMENTS 3,835,864 A    9/1974 Rasor et al.
3,943,936 A    3/1976 Rasor
(Continued)

FOREIGN PATENT DOCUMENTS

AU    2008279789 B2    10/2011
EP    0362611 A1    4/1990
(Continued)

OTHER PUBLICATIONS

Hachisuka et al., "Development and Performance Analysis of an Intra-Body Communication Device," The 12th International Conference on Solid State Sensors, Actuators and Microsystems, vol. 4A1.3, pp. 1722-1725, 2003.
(Continued)

*Primary Examiner* — Kennedy Schaetzle
(74) *Attorney, Agent, or Firm* — Seager, Tufte & Wickhem LLP

(57) ABSTRACT

Systems and methods for communicating between medical devices. In one example, a method for communicating between a plurality of medical devices in a medical device system comprises, with a first medical device, communicating a first message to a second medical device. The method further comprises, with the second medical device, receiving the first message, wherein the first message comprises a plurality of communication pulses. A first set of the plurality of communication pulses represent a synchronization portion of the first message. A second set of the plurality of communication pulses represent a relative device address portion of the first message. A third set of the plurality of communication pulses represent a command portion of the
(Continued)

first message. A fourth set of the plurality of communication pulses represent a payload portion of the first message.

17 Claims, 15 Drawing Sheets

Related U.S. Application Data on Aug. 6, 2014, provisional application No. 62/033,978, filed on Aug. 6, 2014, provisional application No. 62/033,998, filed on Aug. 6, 2014.

(51) Int. Cl.
  *A61N 1/39* (2006.01)
  *G06F 19/00* (2011.01)
  *H04L 7/04* (2006.01)
  *H04L 27/02* (2006.01)
  *A61B 5/00* (2006.01)

(52) U.S. Cl.
  CPC ............ *G06F 19/3418* (2013.01); *H04L 7/04* (2013.01); *H04L 27/02* (2013.01); *A61B 5/0024* (2013.01); *A61B 5/0028* (2013.01)

(56) References Cited

U.S. PATENT DOCUMENTS

| | | | |
|---|---|---|---|
| 4,151,513 A | 4/1979 | Menken et al. | |
| 4,157,720 A | 6/1979 | Greatbatch | |
| 4,256,115 A | 3/1981 | Bilitch | |
| 4,312,354 A | 1/1982 | Walters | |
| 4,440,173 A | 4/1984 | Hudziak et al. | |
| 4,522,208 A | 6/1985 | Buffet | |
| 4,793,353 A | 12/1988 | Borkan | |
| 4,987,897 A | 1/1991 | Funke | |
| 4,989,602 A | 2/1991 | Sholder et al. | |
| 5,012,806 A | 5/1991 | De Bellis | |
| 5,058,581 A | 10/1991 | Silvian | |
| 5,109,845 A | 5/1992 | Yuuchi et al. | |
| 5,113,859 A | 5/1992 | Funke | |
| 5,331,966 A | 7/1994 | Bennett et al. | |
| 5,342,408 A | 8/1994 | deCoriolis et al. | |
| 5,404,877 A | 4/1995 | Nolan et al. | |
| 5,411,535 A | 5/1995 | Fujii et al. | |
| 5,741,314 A | 4/1998 | Daly et al. | |
| 5,752,977 A * | 5/1998 | Grevious ............ | A61N 1/3727 607/32 |
| 5,792,202 A | 8/1998 | Rueter | |
| 5,792,205 A | 8/1998 | Alt et al. | |
| 5,814,089 A | 9/1998 | Stokes et al. | |
| 5,842,977 A | 12/1998 | Lesho et al. | |
| 5,899,876 A | 5/1999 | Flower | |
| 5,899,928 A | 5/1999 | Sholder et al. | |
| 5,935,078 A | 8/1999 | Feierbach | |
| 5,941,906 A | 8/1999 | Barreras, Sr. et al. | |
| 5,999,848 A * | 12/1999 | Gord ................... | A61B 5/14865 607/2 |
| 5,999,857 A | 12/1999 | Weijand et al. | |
| 6,076,016 A | 6/2000 | Feierbach | |
| 6,080,187 A | 6/2000 | Alt et al. | |
| 6,115,636 A | 9/2000 | Ryan | |
| 6,141,588 A | 10/2000 | Cox et al. | |
| 6,141,592 A | 10/2000 | Pauly | |
| 6,144,879 A | 11/2000 | Gray | |
| 6,164,284 A | 12/2000 | Schulman et al. | |
| 6,208,894 B1 | 3/2001 | Schulman et al. | |
| 6,211,799 B1 | 4/2001 | Post et al. | |
| 6,266,558 B1 | 7/2001 | Gozani et al. | |
| 6,409,674 B1 | 6/2002 | Brockway et al. | |
| 6,438,417 B1 | 8/2002 | Rockwell et al. | |
| 6,441,747 B1 | 8/2002 | Khair et al. | |
| 6,453,200 B1 | 9/2002 | Koslar | |
| 6,471,645 B1 | 10/2002 | Warkentin et al. | |
| 6,507,755 B1 | 1/2003 | Gozani et al. | |
| 6,561,975 B1 | 5/2003 | Pool et al. | |
| 6,584,352 B2 | 6/2003 | Combs et al. | |
| 6,597,948 B1 | 7/2003 | Rockwell et al. | |
| 6,628,985 B2 | 9/2003 | Sweeney et al. | |
| 6,689,117 B2 | 2/2004 | Sweeney et al. | |
| 6,690,959 B2 | 2/2004 | Thompson | |
| 6,704,602 B2 | 3/2004 | Berg et al. | |
| 6,738,670 B1 | 5/2004 | Almendinger et al. | |
| 6,749,566 B2 | 6/2004 | Russ | |
| 6,758,810 B2 | 7/2004 | Lebel et al. | |
| 6,763,269 B2 | 7/2004 | Cox | |
| 6,804,558 B2 | 10/2004 | Haller et al. | |
| 6,847,844 B2 | 1/2005 | Sun et al. | |
| 6,897,788 B2 | 5/2005 | Khair et al. | |
| 6,904,315 B2 | 6/2005 | Panken et al. | |
| 6,947,795 B2 * | 9/2005 | Bornhoft ................. | G08C 19/24 375/239 |
| 6,957,107 B2 | 10/2005 | Rogers et al. | |
| 7,013,178 B2 | 3/2006 | Reinke et al. | |
| 7,027,871 B2 | 4/2006 | Burnes et al. | |
| 7,060,031 B2 | 6/2006 | Webb et al. | |
| 7,110,824 B2 | 9/2006 | Amundson et al. | |
| 7,139,613 B2 | 11/2006 | Reinke et al. | |
| 7,149,581 B2 | 12/2006 | Goedeke | |
| 7,162,307 B2 | 1/2007 | Patrias | |
| 7,177,700 B1 | 2/2007 | Cox | |
| 7,181,505 B2 | 2/2007 | Haller et al. | |
| 7,200,437 B1 | 4/2007 | Nabutovsky et al. | |
| 7,200,439 B2 | 4/2007 | Zdeblick et al. | |
| 7,206,423 B1 | 4/2007 | Feng et al. | |
| 7,209,790 B2 | 4/2007 | Thompson et al. | |
| 7,228,183 B2 | 6/2007 | Sun et al. | |
| 7,236,821 B2 | 6/2007 | Cates et al. | |
| 7,254,448 B2 | 8/2007 | Almendinger et al. | |
| 7,260,436 B2 | 8/2007 | Kilgore et al. | |
| 7,277,755 B1 | 10/2007 | Falkenberg et al. | |
| 7,280,872 B1 | 10/2007 | Mosesov et al. | |
| 7,289,852 B2 | 10/2007 | Helfinstine et al. | |
| 7,289,853 B1 | 10/2007 | Campbell et al. | |
| 7,289,855 B2 | 10/2007 | Nghiem et al. | |
| 7,305,266 B1 | 12/2007 | Kroll | |
| 7,347,819 B2 | 3/2008 | Lebel et al. | |
| 7,366,572 B2 | 4/2008 | Heruth et al. | |
| 7,384,403 B2 | 6/2008 | Sherman | |
| 7,386,342 B1 | 6/2008 | Falkenberg et al. | |
| 7,392,090 B2 | 6/2008 | Sweeney et al. | |
| 7,406,105 B2 | 7/2008 | DelMain et al. | |
| 7,406,349 B2 | 7/2008 | Seeberger et al. | |
| 7,425,200 B2 | 9/2008 | Brockway et al. | |
| 7,502,652 B2 | 3/2009 | Gaunt et al. | |
| 7,512,448 B2 | 3/2009 | Malick et al. | |
| 7,532,933 B2 | 5/2009 | Hastings et al. | |
| 7,539,541 B2 | 5/2009 | Quiles et al. | |
| 7,558,631 B2 | 7/2009 | Cowan et al. | |
| 7,565,195 B1 | 7/2009 | Kroll et al. | |
| 7,584,002 B2 | 9/2009 | Burnes et al. | |
| 7,590,455 B2 | 9/2009 | Heruth et al. | |
| 7,610,092 B2 | 10/2009 | Cowan et al. | |
| 7,610,099 B2 | 10/2009 | Almendinger et al. | |
| 7,616,991 B2 | 11/2009 | Mann et al. | |
| 7,617,001 B2 | 11/2009 | Penner et al. | |
| 7,630,767 B1 | 12/2009 | Poore et al. | |
| 7,634,313 B1 | 12/2009 | Kroll et al. | |
| 7,637,867 B2 | 12/2009 | Zdeblick | |
| 7,640,060 B2 | 12/2009 | Zdeblick | |
| 7,647,109 B2 | 1/2010 | Hastings et al. | |
| 7,650,186 B2 | 1/2010 | Hastings et al. | |
| 7,668,596 B2 | 2/2010 | Von Arx et al. | |
| 7,713,194 B2 | 5/2010 | Zdeblick | |
| 7,713,195 B2 | 5/2010 | Zdeblick | |
| 7,738,958 B2 | 6/2010 | Zdeblick et al. | |
| 7,738,964 B2 | 6/2010 | Von Arx et al. | |
| 7,742,816 B2 | 6/2010 | Masoud et al. | |
| 7,742,822 B2 | 6/2010 | Masoud et al. | |

(56) References Cited

U.S. PATENT DOCUMENTS

| | | | |
|---|---|---|---|
| 7,743,151 B2 | 6/2010 | Vallapureddy et al. |
| 7,761,164 B2 | 7/2010 | Verhoef et al. |
| 7,765,001 B2 | 7/2010 | Echt et al. |
| 7,792,588 B2 | 9/2010 | Harding |
| 7,801,596 B2 | 9/2010 | Fischell et al. |
| 7,860,455 B2 | 12/2010 | Fukumoto et al. |
| 7,881,798 B2 | 2/2011 | Miesel et al. |
| 7,890,181 B2 | 2/2011 | Denzene et al. |
| 7,894,894 B2 | 2/2011 | Stadler et al. |
| 7,894,907 B2 | 2/2011 | Cowan et al. |
| 7,894,915 B1 | 2/2011 | Chitre et al. |
| 7,904,170 B2 | 3/2011 | Harding |
| 7,907,993 B2 | 3/2011 | Ghanem et al. |
| 7,925,343 B1 | 4/2011 | Min et al. |
| 7,937,148 B2 | 5/2011 | Jacobson |
| 7,945,333 B2 | 5/2011 | Jacobson |
| 7,946,997 B2 | 5/2011 | Hübinette |
| 7,949,404 B2 | 5/2011 | Hill |
| 7,949,405 B2 | 5/2011 | Feher |
| 7,974,702 B1 | 7/2011 | Fain et al. |
| 7,979,136 B2 | 7/2011 | Young et al. |
| 7,983,753 B2 | 7/2011 | Severin |
| 7,991,467 B2 | 8/2011 | Markowitz et al. |
| 7,996,087 B2 | 8/2011 | Cowan et al. |
| 8,000,791 B2 | 8/2011 | Sunagawa et al. |
| 8,001,975 B2 | 8/2011 | DiSilvestro et al. |
| 8,002,700 B2 | 8/2011 | Ferek-Petric et al. |
| 8,010,209 B2 | 8/2011 | Jacobson |
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,046,079 B2 | 10/2011 | Bange et al. |
| 8,046,080 B2 | 10/2011 | Von Arx et al. |
| 8,050,297 B2 | 11/2011 | DelMain et al. |
| 8,050,759 B2 | 11/2011 | Stegemann et al. |
| 8,055,345 B2 | 11/2011 | Li et al. |
| 8,055,350 B2 | 11/2011 | Roberts |
| 8,060,212 B1 | 11/2011 | Rios et al. |
| 8,065,018 B2 | 11/2011 | Haubrich et al. |
| 8,073,542 B2 | 12/2011 | Doerr |
| 8,078,278 B2 | 12/2011 | Penner |
| 8,095,123 B2 | 1/2012 | Gray |
| 8,102,789 B2 | 1/2012 | Rosar et al. |
| 8,114,021 B2 | 2/2012 | Robertson et al. |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,150,521 B2 | 4/2012 | Crowley et al. |
| 8,160,672 B2 | 4/2012 | Kim et al. |
| 8,160,702 B2 | 4/2012 | Mann et al. |
| 8,160,704 B2 | 4/2012 | Freeberg |
| 8,175,715 B1 | 5/2012 | Cox |
| 8,180,451 B2 | 5/2012 | Hickman et al. |
| 8,187,161 B2 | 5/2012 | Li et al. |
| 8,209,014 B2 | 6/2012 | Doerr |
| 8,214,043 B2 | 7/2012 | Matos |
| 8,224,244 B2 | 7/2012 | Kim et al. |
| 8,233,985 B2 | 7/2012 | Bulkes et al. |
| 8,265,748 B2 | 9/2012 | Liu et al. |
| 8,265,757 B2 | 9/2012 | Mass et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,021 B2 | 11/2012 | Kisker et al. |
| 8,321,036 B2 | 11/2012 | Brockway et al. |
| 8,332,036 B2 | 12/2012 | Hastings et al. |
| 8,335,568 B2 | 12/2012 | Heruth et al. |
| 8,340,780 B2 | 12/2012 | Hastings et al. |
| 8,352,025 B2 | 1/2013 | Jacobson |
| 8,352,038 B2 | 1/2013 | Mao et al. |
| 8,369,959 B2 | 2/2013 | Meskens |
| 8,369,962 B2 | 2/2013 | Abrahamson |
| 8,380,320 B2 | 2/2013 | Spital |
| 8,386,051 B2 | 2/2013 | Rys |
| 8,391,981 B2 | 3/2013 | Mosesov |
| 8,406,874 B2 | 3/2013 | Liu et al. |
| 8,406,886 B2 | 3/2013 | Gaunt et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,722 B2 | 4/2013 | Verhoef et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,761 B2 | 6/2013 | Wariar |
| 8,571,678 B2 | 10/2013 | Wang |
| 8,744,572 B1 | 6/2014 | Greenhut et al. |
| 2004/0167587 A1 | 8/2004 | Thompson |
| 2004/0172104 A1 | 9/2004 | Berg et al. |
| 2006/0241705 A1 | 10/2006 | Neumann et al. |
| 2007/0088394 A1* | 4/2007 | Jacobson ............ A61N 1/3925 607/4 |
| 2007/0088396 A1 | 4/2007 | Jacobson |
| 2007/0088397 A1 | 4/2007 | Jacobson |
| 2007/0233206 A1 | 10/2007 | Frikart et al. |
| 2008/0021519 A1 | 1/2008 | De Geest et al. |
| 2008/0228234 A1 | 9/2008 | Stancer |
| 2008/0294210 A1 | 11/2008 | Rosero |
| 2008/0306359 A1 | 12/2008 | Zdeblick et al. |
| 2009/0088813 A1 | 4/2009 | Brockway et al. |
| 2009/0135886 A1 | 5/2009 | Robertson et al. |
| 2009/0216292 A1 | 8/2009 | Pless et al. |
| 2010/0023085 A1 | 1/2010 | Wu et al. |
| 2010/0056871 A1 | 3/2010 | Govari et al. |
| 2010/0114209 A1 | 5/2010 | Krause et al. |
| 2010/0198304 A1 | 8/2010 | Wang |
| 2010/0228308 A1 | 9/2010 | Cowan et al. |
| 2011/0022113 A1 | 1/2011 | Zdeblick et al. |
| 2011/0071586 A1 | 3/2011 | Jacobson |
| 2011/0077708 A1 | 3/2011 | Ostroff |
| 2011/0152970 A1 | 6/2011 | Jollota et al. |
| 2011/0184491 A1 | 7/2011 | Kivi |
| 2011/0208260 A1 | 8/2011 | Jacobson |
| 2011/0218587 A1 | 9/2011 | Jacobson |
| 2011/0230734 A1 | 9/2011 | Fain et al. |
| 2012/0004527 A1 | 1/2012 | Thompson et al. |
| 2012/0093245 A1 | 4/2012 | Makdissi et al. |
| 2012/0109236 A1 | 5/2012 | Jacobson et al. |
| 2012/0109259 A1 | 5/2012 | Bond et al. |
| 2012/0172942 A1 | 7/2012 | Berg |
| 2012/0197350 A1 | 8/2012 | Roberts |
| 2012/0215285 A1 | 8/2012 | Tahmasian et al. |
| 2012/0296381 A1 | 11/2012 | Matos |
| 2012/0316613 A1 | 12/2012 | Keefe et al. |
| 2013/0012151 A1 | 1/2013 | Hankins |
| 2013/0041422 A1 | 2/2013 | Jacobson |
| 2013/0053908 A1 | 2/2013 | Smith et al. |
| 2013/0066169 A1 | 3/2013 | Rys et al. |
| 2013/0072770 A1 | 3/2013 | Rao et al. |
| 2013/0085550 A1 | 4/2013 | Polefko et al. |
| 2013/0096649 A1 | 4/2013 | Martin et al. |
| 2013/0103109 A1 | 4/2013 | Jacobson |
| 2013/0110008 A1 | 5/2013 | Bourget et al. |
| 2014/0214104 A1 | 7/2014 | Greenhut et al. |

FOREIGN PATENT DOCUMENTS

| | | | |
|---|---|---|---|
| EP | 1702648 A2 | 9/2006 |

(56) References Cited

FOREIGN PATENT DOCUMENTS

EP     2433675 B1     1/2013
EP     2441491 B1     1/2013

OTHER PUBLICATIONS

Seyedi et al., "A Survey on Intrabody Communications for Body Area Network Application," IEEE, pp. 1-13, 2013.
Wegmüller, "Intra-Body Communication for Biomedical Sensor Networks," Diss. ETH, No. 17323, 1-173, 2007.

* cited by examiner

METHOD AND APPARATUS FOR COMMUNICATING BETWEEN MEDICAL DEVICES

CROSS-REFERENCES TO RELATED APPLICATIONS

This application claims the benefit of U.S. Provisional Application No. 62/034,017, filed Aug. 6, 2014, U.S. Provisional Application No. 62/033,932, filed Aug. 6, 2014, U.S. Provisional Application No. 62/033,978, filed Aug. 6, 2014, and U.S. Provisional Application No. 62/033,998, filed Aug. 6, 2014, the complete disclosures of which are herein incorporated by reference.

TECHNICAL FIELD

The present disclosure generally relates to medical devices, and more particularly to communications between medical devices in a multi-device system.

BACKGROUND

Pacing instruments can be used to treat patients suffering from various heart conditions that may result in a reduced ability of the heart to deliver sufficient amounts of blood to a patient's body. These heart conditions may lead to rapid, irregular, and/or inefficient heart contractions. To help alleviate some of these conditions, various devices (e.g., pacemakers, defibrillators, etc.) can be implanted in a patient's body. Such devices may monitor and provide electrical stimulation to the heart to help the heart operate in a more normal, efficient and/or safe manner. In some cases, a patient may have multiple implanted devices, including devices that are intended to treat other parts of the body.

SUMMARY

The present disclosure relates generally to systems and methods for coordinating treatment of abnormal heart activity using multiple implanted devices within a patient. It is contemplated that the multiple implanted devices may include, for example, pacemakers, defibrillators, diagnostic devices, and/or any other suitable implantable devices, as desired.

In a first example, a method for communicating between a plurality of medical devices in a medical device system comprises: with a first medical device, communicating a first message to a second medical device; with the second medical device, receiving the first message, wherein the first message comprises a plurality of communication pulses, wherein: a first set of the plurality of communication pulses represent a synchronization portion of the first message; a second set of the plurality of communication pulses represent a relative device address portion of the first message; a third set of the plurality of communication pulses represent a command portion of the first message; and a fourth set of the plurality of communication pulses represent a payload portion of the first message.

Alternatively, or additionally, in any of the above examples, the synchronization portion of the first message indicates a beginning of the first message.

Alternatively, or additionally, in any of the above examples, the relative device address portion of the first message, the command portion of the first message and the payload portion of the first message follow the synchronization portion of the first message.

Alternatively, or additionally, in any of the above examples, the relative device address portion of the first message precedes the command portion of the first message.

Alternatively, or additionally, in any of the above examples, the relative device address portion of the first message contains a relative device address.

Alternatively, or additionally, in any of the above examples, the relative device address corresponds to either a single device of the medical device system or all of the devices of the medical device system.

Alternatively, or additionally, in any of the above examples, the command portion of the first message contains a command, wherein the command is one of: a read command for reading data; a write command for writing data; a pairing command for pairing the first medical device and the second medical device; and a ping command.

Alternatively, or additionally, in any of the above examples, the payload portion of the command comprises data and/or an address.

Alternatively, or additionally, in any of the above examples, a fifth set of the plurality of communication pulses represent an error check portion of the first message.

Alternatively, or additionally, in any of the above examples, the error check portion of the first message contains a cyclic redundancy check code.

Alternatively, or additionally, in any of the above examples, the plurality of communication pulses are sub-threshold communication pulses that are below a capture threshold of the heart.

Alternatively, or additionally, any of the above examples may further comprise: with the second medical device, communicating a second message to the first medical device; with the first medical device, receiving the second message, wherein the second message comprises a plurality of communication pulses; and wherein each of the plurality of communication pulses of the first message have a first pulse energy, and each of the plurality of communication pulses of the second message have a second pulse energy, wherein the first pulse energy is different from the second pulse energy.

Alternatively, or additionally, in any of the above examples, the difference between the first pulse energy and the second pulse energy is due to at least one of a difference in pulse width and a difference in pulse amplitude.

Alternatively, or additionally, in any of the above examples, the second pulse energy is greater than the first pulse energy.

Alternatively, or additionally, in any of the above examples, the second pulse energy is at least 5 times greater than the first pulse energy.

Alternatively, or additionally, in any of the above examples, the first message is communicated through body tissue via conducted communication.

Alternatively, or additionally, in any of the above examples, the first medical device is an implantable subcutaneous cardioverter and the second medical device is an implantable leadless cardiac pacemaker.

In another example, a first implantable medical device comprises: a communication module for communicating by conducted communication with a second implantable medical device; a controller operatively coupled to the communication module, the controller configured to transmit a first message, wherein the first message comprises a plurality of communication pulses, wherein: a first set of the plurality of communication pulses represent a synchronization portion of the first message; a second set of the plurality of communication pulses represent a relative device address portion of the first message; a third set of the plurality of communication pulses represent a command portion of the first message; and a fourth set of the plurality of communication pulses represent a payload portion of the first message.

Alternatively, or additionally, the controller may further be configured to transmit the first message in a manner consistent with or with features consistent with any of the above described examples with respect to communicating between a plurality of medical devices.

Alternatively, or additionally, in any of the above examples, the first implantable medical device comprises an implantable subcutaneous cardioverter, and the second implantable medical device comprises an implantable leadless cardiac pacemaker.

In yet another example, a medical system comprises: a first implantable medical device; a second implantable medical device; wherein the first implantable medical device is configured to send a first message from the first implantable medical device to the second implantable medical device, wherein the first message comprises a plurality of spaced communication pulses each having a first pulse width; wherein the second implantable medical device is configured to send a second message from the second implantable medical device to the first implantable medical device, wherein the second message comprises a plurality of spaced communication pulses each having a second pulse width, wherein the second pulse width is at least two times longer than the first pulse width. In this example, at least one of the first medical device and the second medical device may be of the type of the first implantable medical device described in previous examples. The medical system may, in particular, be used for performing the methods described in previous examples.

Alternatively, or additionally, in any of the above examples, the first implantable medical device comprises an implantable subcutaneous cardioverter, and the second implantable medical device comprises an implantable leadless cardiac pacemaker.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which.

Figure 1:
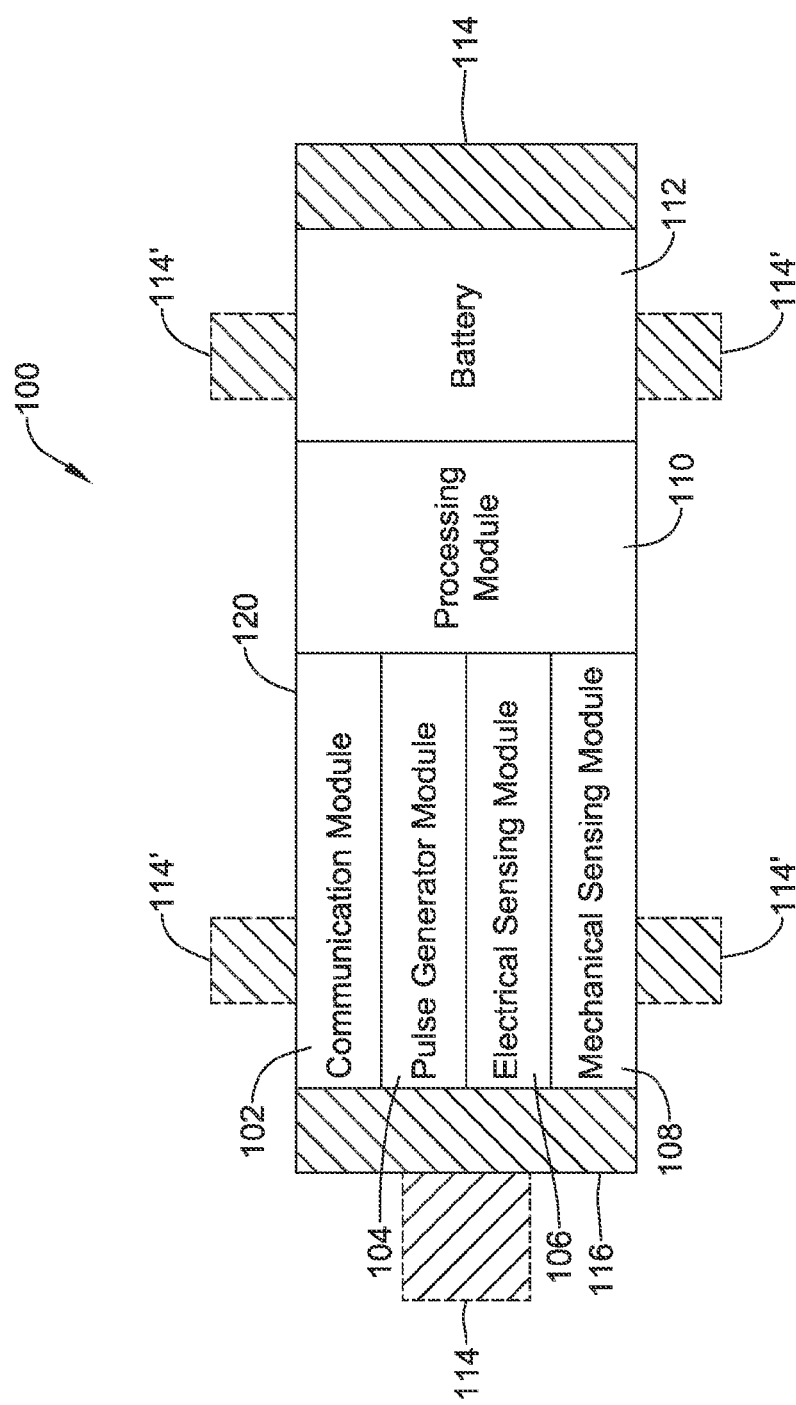
FIG. 1 illustrates a block diagram of an exemplary leadless cardiac pacemaker (LCP) having electrodes, according to one example of the present disclosure.

While the disclosure is amenable to various modifications and alternative forms, specifics thereof have been shown by way of example in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure.

A normal, healthy heart induces contraction by conducting intrinsically generated electrical signals throughout the heart. These intrinsic signals cause the muscle cells or tissue of the heart to contract. This contraction forces blood out of and into the heart, providing circulation of the blood throughout the rest of the body. However, many patients suffer from cardiac conditions that affect this contractility of their hearts. For example, some hearts may develop diseased tissues that no longer generate or conduct intrinsic electrical signals. Such patients may need a medical device to provide pacing therapy to their heart in order to cause their heart to contract and pump blood.

FIGS. 1-4 generally depict implantable medical devices that may be used in systems for delivering pacing therapy, for example including pacing pulses, to a heart of a patient. Some systems may include a plurality of medical devices, such as those described with respect to FIGS. 1-4, which may coordinate to deliver pacing therapy to a heart. While medical devices configured to deliver therapy to the heart of a patient are used as an example multi-device system, the present disclosure should not be so limited. Other multi-device systems are contemplated including systems that have an implantable neuro-stimulator, an implantable sense-only device, and/or any other suitable medical device as desired. This disclosure describes techniques for communicating between devices of such multi-device systems.

FIG. 1 depicts an exemplary leadless cardiac pacemaker (LCP) that may be implanted into a patient and may operate to deliver one or more types of pacing therapy to the heart of the patient, for example by appropriately delivering pacing pulses. In some examples, the LCP may deliver pacing pulses in accordance with one or more therapy techniques, such as bradycardia therapy, rate responsive pacing therapy, anti-tachycardia pacing (ATP) therapy, cardiac resynchronization therapy (CRT), defibrillation therapy, and/or the like. As can be seen in FIG. 1, LCP 100 may be a compact device with all components housed within LCP 100 or directly on housing 120. As shown in the example of FIG. 1, LCP 100 may include communication module 102, pulse generator module 104, electrical sensing module 106, mechanical sensing module 108, processing module 110, battery 112, and electrodes 114.

Communication module 102 may be configured to communicate with devices such as sensors, other medical devices, or the like, that are located externally to LCP 100. Such devices may be located either external or internal to the patient's body. Irrespective of the location, external devices (i.e. external to the LCP 100 but not necessarily external to the patient's body) can communicate with LCP 100 via communication module 102 to accomplish one or more desired functions. For example, LCP 100 may communicate information, such as sensed electrical signals, instructions, other messages, and/or data to an external medical device through communication module 102. The external medical device may use the communicated data and/or messages to perform various functions, such as determining occurrences of arrhythmias, delivering electrical stimulation therapy, storing received data, and/or other functions. LCP 100 may additionally receive instructions, data, and/or other messages from the external medical device through communication module 102, and LCP 100 may use the received instructions, data, and/or other messages to perform various functions, such as determining occurrences of arrhythmias, delivering electrical stimulation therapy, storing received data, and/or other functions. Communication module 102 may be configured to use one or more methods for communicating with external devices. For example, communication module 102 may communicate via conducted communication signals, radiofrequency (RF) signals, inductive coupling, optical signals, acoustic signals and/or any other signals suitable for communication. Illustrative communication techniques between LCP 100 and other devices will be discussed in further detail with reference to other Figures.

In the example shown, pulse generator module 104 may be electrically connected to one or more electrodes 114. In some examples, LCP 100 may additionally include electrodes 114'. In such examples, pulse generator module 104 may additionally be electrically connected to one or more electrodes 114'. Pulse generator module 104 may be configured to generate electrical stimulation signals, such as pacing pulses. For example, pulse generator module 104 may generate electrical stimulation signals by using energy stored in battery 112 within LCP 100 and deliver the generated electrical stimulation signals to tissues of a patient via electrodes 114 and/or 114'. In at least some examples, pulse generator module 104 or LCP 100 may further include switching circuitry to selectively connect one or more of electrodes 114 and/or 114' to pulse generator module 104 in order to select via which electrodes 114/114' pulse generator 104 delivers the electrical stimulation signals. Pulse generator module 104 may generate electrical stimulation signals with particular features or in particular sequences in order to provide one or multiple of a number of different electrical stimulation therapies. For example, pulse generator module 104 may be configured to generate electrical stimulation signals to provide electrical stimulation therapy to combat bradycardia arrhythmias, tachyarrhythmia arrhythmias, fibrillation arrhythmias, and/or cardiac synchronization arrhythmias. In other examples, pulse generator module 104 may be configured to generate electrical stimulation signals to provide electrical stimulation therapies different than those described herein to treat one or more detected cardiac arrhythmias.

In some examples, LCP 100 may include electrical sensing module 106 and mechanical sensing module 108. Electrical sensing module 106 may be configured to sense the electrical cardiac activity of the heart. For example, electrical sensing module 106 may be connected to one or more electrodes 114/114' and electrical sensing module 106 may be configured to receive electrical cardiac signals conducted through electrodes 114/114'. In some examples, the electrical cardiac signals may represent local information from the chamber in which LCP 100 is implanted. For instance, if LCP 100 is implanted within a ventricle of the heart, electrical cardiac signals sensed by LCP 100 through electrodes 114/114' may represent ventricular electrical cardiac signals. Mechanical sensing module 108 may include, or be electrically connected to, various sensors, such as accelerometers, blood pressure sensors, heart sound sensors, blood-oxygen sensors, and/or other sensors which measure one or more physiological parameters of the heart and/or patient. Both electrical sensing module 106 and mechanical sensing module 108 may be further connected to processing module 110, and may provide signals representative of the sensed electrical cardiac activity and/or physiological parameters to processing module 110. Although described with respect to FIG. 1 as separate sensing modules, in some examples, electrical sensing module 106 and mechanical sensing module 108 may be combined into a single module.

In some instances, processing module 110 may be configured to control the operation of LCP 100. For example, processing module 110 may be configured to receive electrical cardiac signals from electrical sensing module 106 and/or physiological parameters from mechanical sensing module 108. Based on the received signals, processing module 110 may determine occurrences and types of arrhythmias. Based on any determined arrhythmias, processing module 110 may control pulse generator module 104 to generate electrical stimulation in accordance with one or more electrical stimulation therapies to treat the determined arrhythmias. Processing module 110 may further receive information from communication module 102. In some examples, processing module 110 may use such received information, either instead of or in addition to information received from electrical sensing module 106 and/or mechanical sensing module 108, in determining whether an arrhythmia is occurring, in determining a type of arrhythmia, and/or in determining to take particular action in response to the information. Processing module 110 may additionally control communication module 102 to send information to other devices.

In some examples, processing module 110 may include a pre-programmed chip, such as a very-large-scale integration (VLSI) chip or an application specific integrated circuit (ASIC). In such embodiments, the chip may be pre-programmed with control logic in order to control the operation of LCP 100. By using a pre-programmed chip, processing module 110 may use less power than other programmable circuits while able to maintain basic functionality, thereby increasing the battery life of LCP 100. In other examples, processing module 110 may include a programmable microprocessor or the like. Such a programmable microprocessor may allow a user to adjust the control logic of LCP 100 after manufacture, thereby allowing for greater flexibility of LCP 100 than when using a pre-programmed chip. In some examples, processing module 110 may further include a memory circuit and processing module 110 may store information on and read information from the memory circuit. In other examples, LCP 100 may include a separate memory circuit (not shown) that is in communication with processing module 110, such that processing module 110 may read and write information to and from the separate memory circuit. The memory circuit, whether part of processing module 110 or separate from processing module 110 may have address lengths of, for example, eight bits. However, in other examples, the memory circuit may have address lengths of sixteen, thirty-two, or sixty-four bits, or any other bit length that is suitable. Additionally, the memory circuit may be volatile memory, non-volatile memory, or a combination of both volatile memory and non-volatile memory.

Battery 112 may provide a power source to LCP 100 for its operations. In some examples, battery 112 may be a non-rechargeable lithium-based battery. In other examples, the non-rechargeable battery may be made from other suitable materials known in the art. Because LCP 100 is an implantable device, access to LCP 100 may be limited. In such circumstances, it is necessary to have sufficient battery capacity to deliver therapy over an extended period of treatment such as days, weeks, months, or years. In some examples, battery 110 may a rechargeable battery in order to facilitate increasing the useable lifespan of LCP 100.

As depicted in FIG. 1, LCP 100 may include electrodes 114, which can be secured relative to housing 120 but exposed to the tissue and/or blood surrounding LCP 100. In some cases, electrodes 114 may be generally disposed on either end of LCP 100 and may be in electrical communication with one or more of modules 102, 104, 106, 108, and 110. In some examples, LCP 100 may additionally include one or more electrodes 114'. Electrodes 114' may be positioned on the sides of LCP 100 and increase the number of electrodes by which LCP 100 may sense electrical cardiac activity and/or deliver electrical stimulation. Electrodes 114 and/or 114' can be made up of one or more biocompatible conductive materials such as various metals or alloys that are known to be safe for implantation within a human body. In some instances, electrodes 114 and/or 114' connected to LCP 100 may have an insulative portion that electrically isolates the electrodes 114 from adjacent electrodes, housing 120, and/or other materials. In some cases, electrodes 114 and/or 114' may be spaced from the housing and connected through connecting wires. In such embodiments, the electrodes 114 and/or 114' may be placed on a on a tail that extends from the housing 120.

It is contemplated that electrodes 114 and/or 114' may have any of a variety of sizes and/or shapes, and may be spaced at any of a variety of distances. For example, electrodes 114 may have a diameter of two to twenty millimeters (mm). However, in other examples, electrodes 114 and/or 114' may have a diameter of two, three, five, seven millimeters (mm), or any other suitable diameter, dimension and shape. In some cases, electrodes 114 and/or 114' may have a length of zero, one, three, five, ten millimeters (mm), or any other suitable length, where the length is a dimension of electrodes 114 and/or 114' that extends away from housing 120. Additionally, at least some of electrodes 114 and/or 114' may be spaced from one another by a distance of twenty, thirty, forty, fifty millimeters (mm), or any other suitable distance. The electrodes 114 and/or 114' of a single device may have different sizes with respect to each other, and the spacing of the electrodes on the device may not be uniform.

To implant LCP 100 inside a patient's body, an operator (e.g., a physician, clinician, etc.), may fix LCP 100 to the cardiac tissue of the patient's heart. To facilitate fixation, LCP 100 may include one or more anchors 116. Anchor 116 may include any number of fixation or anchoring mechanisms. For example, anchor 116 may include one or more pins, staples, threads, screws, helix, tines, and/or the like. In some examples, although not shown, anchor 116 may include threads on its external surface that may run along at least a partial length of anchor 116. The threads may provide friction between the cardiac tissue and the anchor to help fix anchor 116 within the cardiac tissue. In other examples, anchor 116 may include other structures such as barbs, spikes, or the like to facilitate engagement with the surrounding cardiac tissue.

Figure 2:
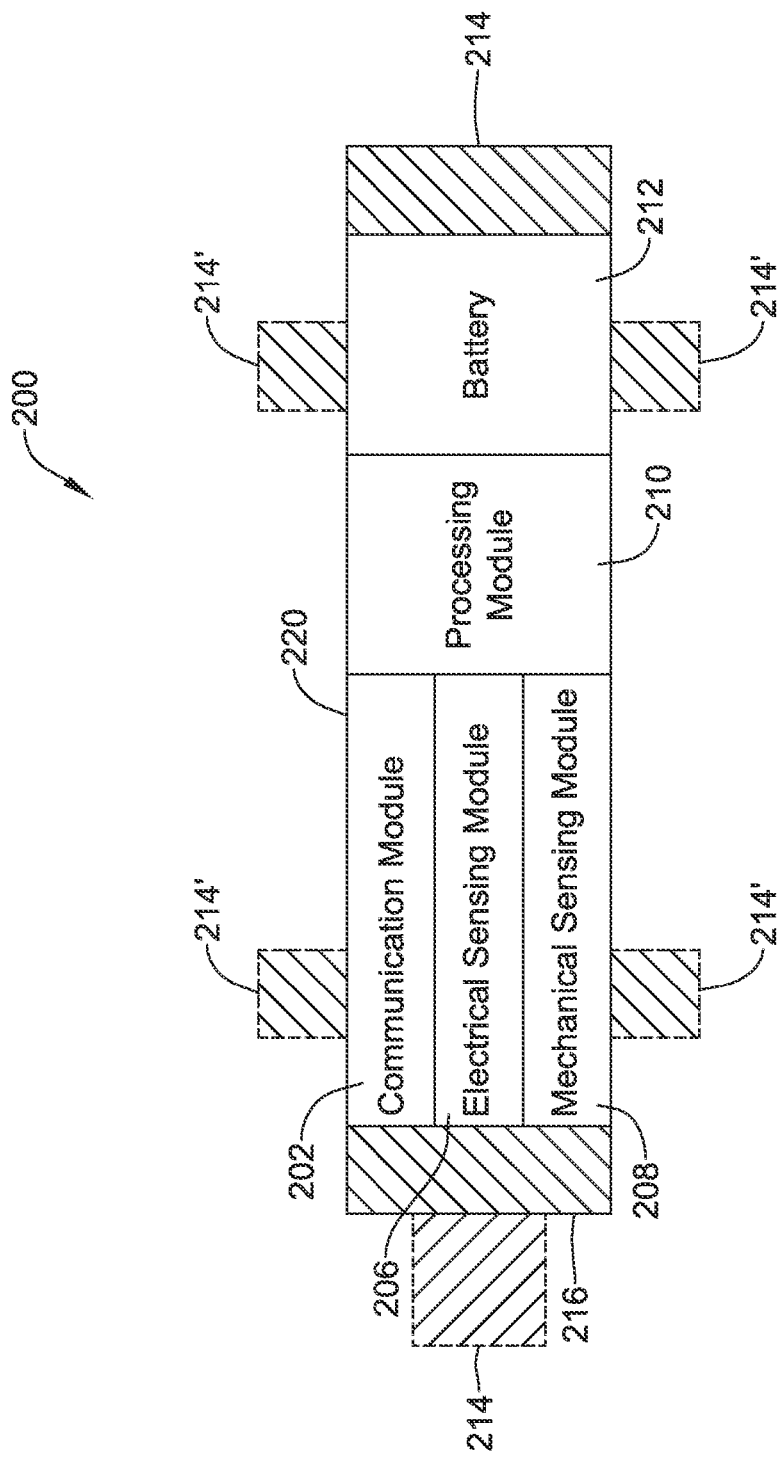
FIG. 2 illustrates a block diagram of an exemplary medical sensing device, according to one example of the present disclosure.

FIG. 2 depicts an exemplary medical device, MD 200, which may be implanted into a patient and may operate to sense one or more signals representative of a physiological condition of the patient. As can be seen in FIG. 2, MD 200 may be a compact device with all components housed within MD 200 or directly on housing 220. As illustrated in FIG. 2, MD 200 may include communication module 202, electrical sensing module 206, mechanical sensing module 208, processing module 210, battery 212, and electrodes 214/214'.

In some examples, MD 200 may be similar to LCP 100 as described with respect to FIG. 1. For example, communication module 202, electrical sensing module 206, mechanical sensing module 208, processing module 210, battery 212, and electrodes 214/214' may be similar to communication module 102, electrical sensing module 106, mechanical sensing module 108, processing module 110, battery 112, and electrodes 114/114', as described with respect to FIG. 1. However, MD 200 may not include a pulse generator module. For instance, MD 200 may be a dedicated sensor device. Accordingly, in some examples, MD 200 may be the same as LCP 100 with a few minor hardware differences. Alternatively, MD 200 may include all of the components of LCP 100, except that one or more of the components may be disabled or not used, such as a pulse generator module.

In other examples, MD 200 may include substantially different hardware than LCP 100. For instance, MD 200 may be substantially different in size than LCP 100, as MD 200 may not require as severe of size constraints as LCP 100 due to typical implant locations for MD 200. In such examples, MD 200 may include a larger battery and/or more powerful processing unit than LCP 100.

Figure 3:
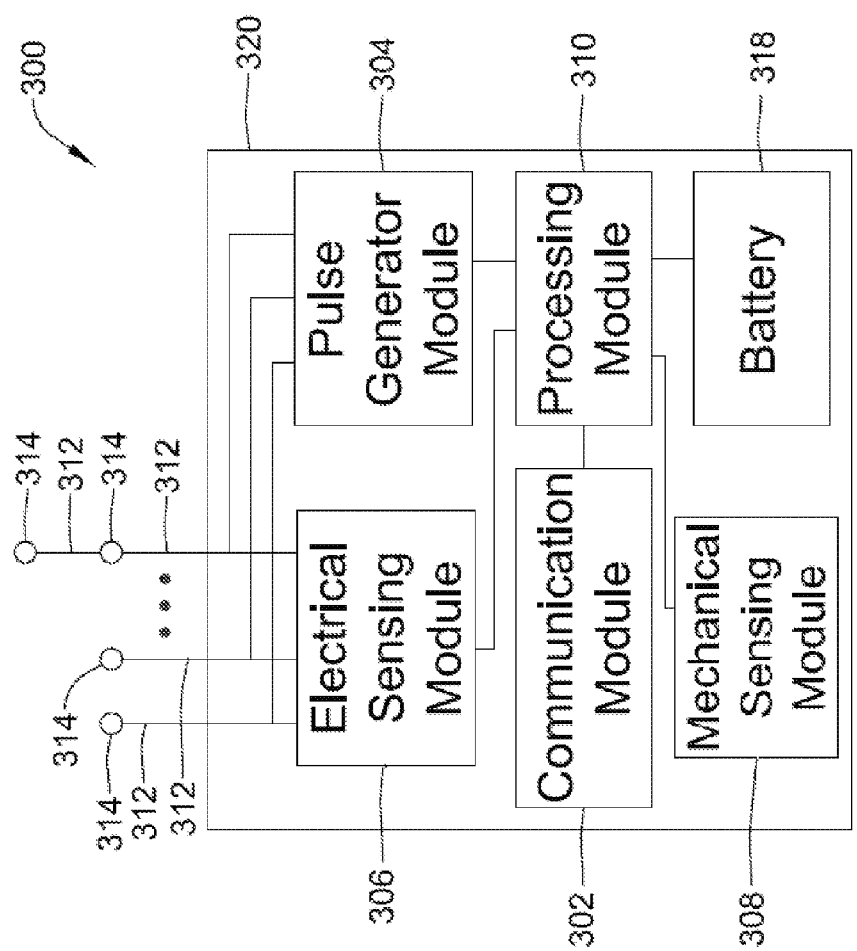
FIG. 3 illustrates a block diagram of an exemplary lead-based medical device, according to one example of the present disclosure.

FIG. 3 depicts an example of another device, medical device (MD) 300, which may be used in conjunction with LCP 100 of FIG. 1 in order to detect and treat cardiac arrhythmias and other heart conditions. In the example shown, MD 300 may include a communication module 302, a pulse generator module 304, an electrical sensing module 306, a mechanical sensing module 308, a processing module 310, and a battery 318. Each of these modules may be similar to modules 102, 104, 106, 108, and 110 of LCP 100. Additionally, battery 318 may be similar to battery 112 of LCP 100. However, in some examples, MD 300 may have a larger volume within housing 320. In such examples, MD 300 may include a larger battery and/or a larger processing module 310 capable of handling more complex operations than processing module 110 of LCP 100.

While MD 300 may be another leadless device such as shown in FIG. 1, in some instances MD 300 may include leads, such as leads 312. Leads 312 may include electrical wires that conduct electrical signals between electrodes 314 and one or more modules located within housing 320. In some cases, leads 312 may be connected to and extend away from housing 320 of MD 300. In some examples, leads are implanted on, within, or adjacent to a heart of a patient. Leads 312 may contain one or more electrodes 314 positioned at various locations on leads 312 and various distances from housing 320. Some leads 312 may only include a single electrode 314, while other leads 312 may include multiple electrodes 314. Generally, electrodes 314 are positioned on leads 312 such that when leads 312 are implanted within the patient, one or more of the electrodes 314 are positioned to perform a desired function. In some cases, the one or more of the electrodes 314 may be in contact with the patient's cardiac tissue. In other cases, one or more of the electrodes 314 may be subcutaneously implanted but adjacent to the patient's heart. Electrodes 314 may conduct intrinsically generated electrical cardiac signals to leads 312. Leads 312 may, in turn, conduct the received electrical cardiac signals to one or more of the modules 302, 304, 306, and 308 of MD 300. In some cases, MD 300 may generate electrical stimulation signals, and leads 312 may conduct the generated electrical stimulation signals to electrodes 314. Electrodes 314 may then conduct the electrical stimulation signals to the cardiac tissue of the patient (either directly or indirectly).

Leads 312 may additionally contain one or more sensors, such as accelerometers, blood pressure sensors, heart sound sensors, blood-oxygen sensors, and/or other sensors which are configured to measure one or more physiological parameters of the heart and/or patient. In such examples, mechanical sensing module 308 may be in electrical communication with leads 312 and may receive signals generated from such sensors.

While not required, in some examples MD 300 may be an implantable medical device. In such examples, housing 320 of MD 300 may be implanted in, for example, a transthoracic region of the patient. Housing 320 may generally include any of a number of known materials that are safe for implantation in a human body and may, when implanted, hermetically seal the various components of MD 300 from fluids and tissues of the patient's body.

In some cases, MD 300 may be an implantable cardiac pacemaker (ICP). In these examples, MD 300 may have one or more leads, for example leads 312, which are implanted on or within the patient's heart. The one or more leads 312 may include one or more electrodes 314 that are in contact with cardiac tissue and/or blood of the patient's heart. MD 300 may be configured to sense intrinsically generated cardiac electrical signals and determine, for example, one or more cardiac arrhythmias based on analysis of the sensed signals. MD 300 may be configured to deliver CRT, ATP therapy, bradycardia therapy, and/or other therapy types via leads 312 implanted within the heart. In some examples, MD 300 may additionally be configured to provide defibrillation therapy.

In some instances, MD 300 may be an implantable cardioverter-defibrillator (ICD). In such examples, MD 300 may include one or more leads implanted within a patient's heart. MD 300 may also be configured to sense electrical cardiac signals, determine occurrences of tachyarrhythmias based on the sensed electrical cardiac signals, and deliver defibrillation therapy in response to determining an occurrence of a tachyarrhythmia. In other examples, MD 300 may be a subcutaneous implantable cardioverter-defibrillator (S-ICD). In examples where MD 300 is an S-ICD, one of leads 312 may be a subcutaneously implanted lead. In at least some examples where MD 300 is an S-ICD, MD 300 may include only a single lead which is implanted subcutaneously but outside of the chest cavity, however this is not required.

In some examples, MD 300 may not be an implantable medical device. Rather, MD 300 may be a device external to the patient's body, and electrodes 314 may be skin-electrodes that are placed on a patient's body. In such examples, MD 300 may be able to sense surface electrical signals (e.g. cardiac electrical signals that are generated by the heart or electrical signals generated by a device implanted within a patient's body and conducted through the body to the skin). In such examples, MD 300 may be configured to deliver various types of electrical stimulation therapy, including, for example, defibrillation therapy.

Figure 4:
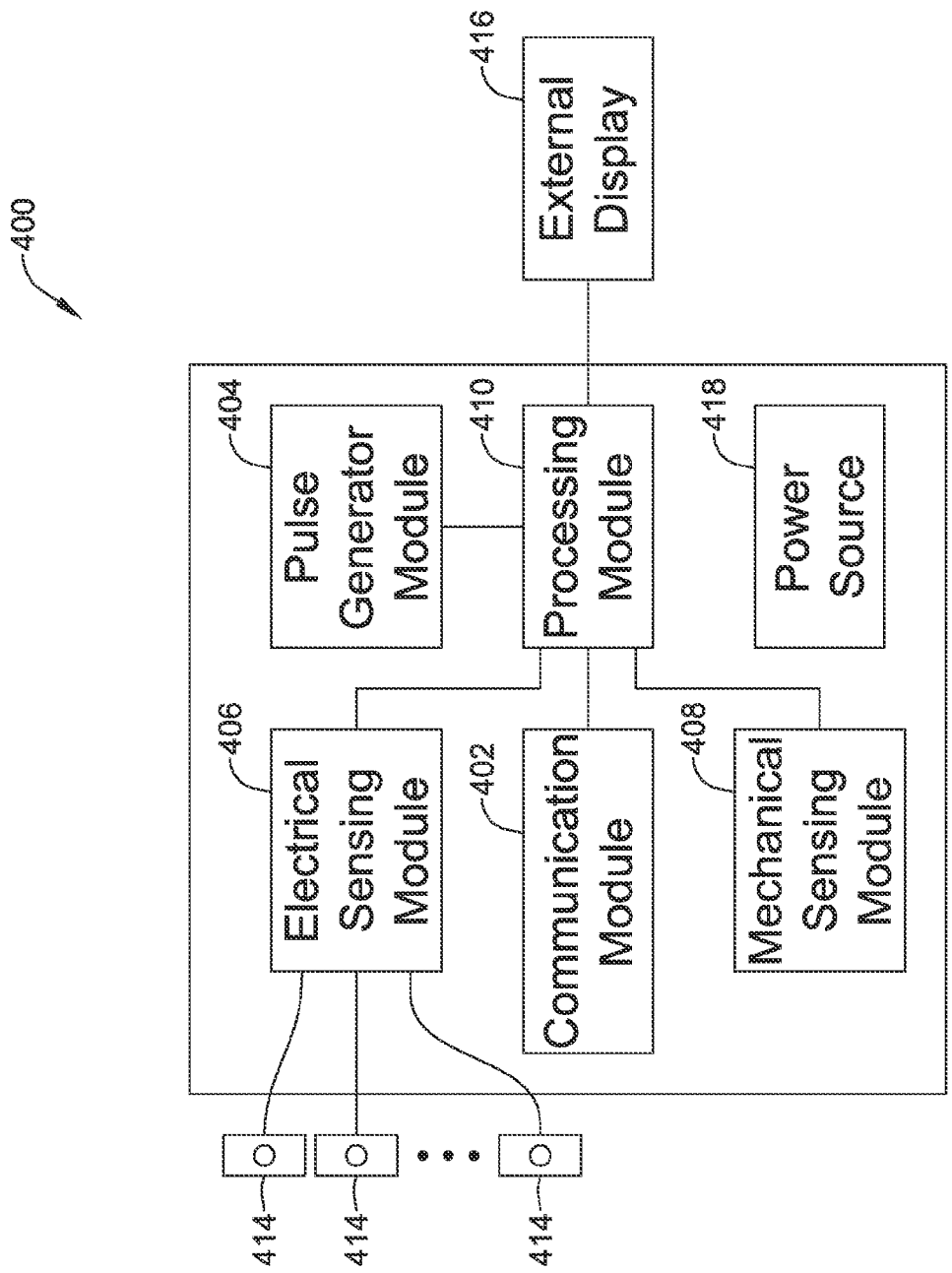
FIG. 4 illustrates a block diagram of an exemplary external medical device, according to one example of the present disclosure.

FIG. 4 depicts an example of another device, medical device (MD) 400, which may be used in conjunction with LCP 100 of FIG. 1 and/or other medical devices in order to detect and treat cardiac arrhythmias and/or other heart conditions. In the example shown, MD 400 may include a communication module 402, a pulse generator module 404, an electrical sensing module 406, a mechanical sensing module 408, a processing module 410, and a power source 418. Each of these modules may be similar to modules 102, 104, 106, 108, and 110 of LCP 100. However, MD 400 may be an external medical device. Accordingly, in some examples, power source 418 may be a power converter that converts externally supplied power, for example from a wall outlet, into a form suitable for MD 400.

MD 400 may additionally include display 416 connected to processing module 410. Display 416 may be a monitor or other screen which is capable of displaying letters, numbers, graphics, and other forms of information. In at least some examples, display 416 may be able to receive user input. For example, display 416 may be a touch sensitive display. In other examples, MD 400 may include one or more peripheral input devices, such as a mouse and/or keyboard. It is contemplated that the display 416 may be incorporated into a common housing with MD 400, or may be in a separate housing.

MD 400 may include electrodes 414. In examples where MD 400 is an external medical device, electrodes 414 include skin patch electrodes. When electrodes 414 are connected to the skin of a patient, MD 400 may sense electrical signals generated within the patient. In an example where MD 400 includes a pulse generator module 404, MD 400 may additionally be able to deliver electrical pulses to the patient through electrodes 414. For example, pulse generator module 404 of MD 400 may be configured to generate electrical stimulation pulses in accordance with one or more electrical stimulation therapies, which are conducted through electrodes 414. Additionally, communication module 402 may be configured to generate conducted communication signals, which are conducted through electrodes 414 and into the body. Mechanical sensing module 408 may include or be connected either directly or communicatively to one or more sensing devices, such as accelerometers, blood pressure sensors, heart sound sensors, blood-oxygen sensors, and other sensors which measure physiological parameters of the heart and/or patient.

In some examples, MD 400 may be a programming device for programming one or more other medical devices, such as those depicted in FIGS. 1-3. In some of these examples, MD 400 may not be configured to deliver electrical stimulation therapies. A user may enter one or more parameters into external display 416 and/or another peripheral device, which sends the entered parameters to processing module 410. In at least some examples, MD 400 may be used to issue an ID (pairing) command to an implantable medical device, as described subsequently with respect to Table 1. Processing module 410 may instruct communication module 402 to communicate the received parameters, or other parameters, to other medical devices using one or more forms of communication, such as conducted communication signals, radiofrequency (RF) signals, inductive coupling, optical signals, acoustic signals, and/or any other suitable signals. Various conducted communication techniques are described herein which communication modules 402 may employ in communicating such parameters and/or other information.

Figure 5:
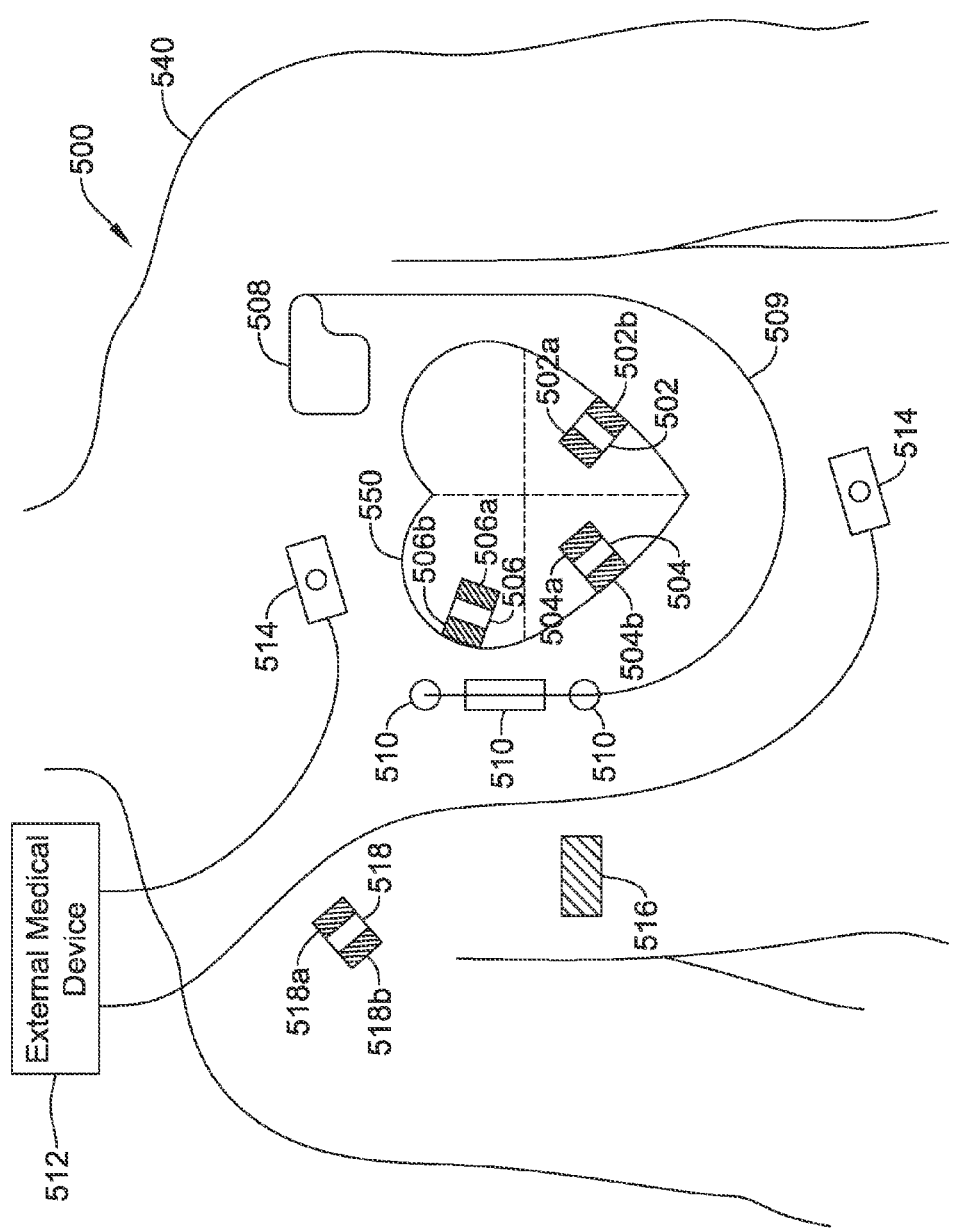
FIG. 5 is a schematic diagram of a system including multiple medical devices, in accordance with examples of the present disclosure.

FIG. 5 illustrates a patient 540 connected to medical device system 500 including devices such as those described with respect to FIGS. 1-4. FIG. 5 illustrates the devices of system 500 implanted or positioned at various example locations. For instance, LCPs 502, 504, 506 are all depicted implanted within a different chamber of heart 550. In some examples, however, the heart may include multiple LCPs implanted within a single chamber, or other LCPs implanted on an external part of heart 550. In still other examples, LCPs may be implanted in other chambers of heart 550 or in different combinations of chambers of heart 550. FIG. 5 also depicts LCP 518 implanted at a location remote from heart 550. An IMD 508 may be a device similar to those described with respect to FIG. 3, such as an ICD, or an S-ICD, with lead 509 connected to electrodes 510 and implanted subcutaneously. A sensor 516 is depicted implanted near the chest of patient 540, and in some cases, may be similar to MD 200 as described with respect to FIG. 2. Sensor 516 may also be implanted at a location remote from the heart. External medical device 512 may not be an implanted medical device. Rather, external medical device 512 may be connected to patient 540 through skin-patch electrodes 514 or the like, and may be similar to MD 400 as described with respect to FIG. 4.

Examples of remote locations for LCP 518 and sensor 516 include devices implanted in the cephalic, cervical, pectoral, thoracic, abdominal, upper limb and lower limb regions of the patient 500. Additionally, remote locations include implant sites within or on an organ or body structure as such locations within or on organs such as the brain, lung, mouth, esophagus, stomach, liver, gallbladder, kidney, pancreas, spleen, intestine, colon, adrenal gland, bladder, uterus, diaphragm, bone. Remote locations also include implant sites in vessels such as blood vessels (e.g. veins, arteries), lymphatic vessels (e.g. jugular trunk, intestinal trunk) and airway vessels (e.g. trachea, bronchi).

The devices of system 500 may communicate via a communication pathway, for example sending and receiving data, instructions, messages and/or other information. Although it is contemplated that the devices may communicate using a variety of modalities, such as with RF signals, inductive coupling, optical signals, or acoustic signals, in at least some examples, the devices of system 500 may communicate using conducted communication. Accordingly, the devices of system 500 may have components that allow for such conducted communication. As discussed above with respect to FIGS. 1-4, the devices of system 500 may each have a communication module. Each communication module may be configured to generate conducted communication signals and transmit the signals into the patient's body via one or more coupled electrodes, such as electrodes 502a, 502b, 504a, 504b, 506a, 506b, 510, 514, 518a, and 518b. Although not depicted specifically in FIG. 5, sensor 516 may also include one or more electrodes. The communication modules may additionally be configured to receive conducted communication signals via the one or more electrodes. In some examples, devices may use a pulse generator module to generate conducted communication signals instead of a communication module.

The patient's body tissue may conduct the conducted communication signals from the transmitting device to a receiving device. In some cases, the conducted communication signals may be galvanically conducted communication signals. For example, a sending device may differentially couple conducted communication signals into the body tissue of patient 540, and the body tissue acts as a transmission line. The receiving device or devices may pick-up these differential signals. This technique is in contrast to capacitive techniques, where transmitted and received signals are referenced to a common ground source.

The conducted communication signals, described in more detail with respect to FIG. 6, may differ from pacing pulses or other electrical stimulation therapy signals. For example, the devices of system 500 may deliver conducted communication signals at an amplitude/pulse width combination that is sub-threshold to the heart so as to not capture the heart. In some cases, the amplitude/pulse width combination of the delivered conducted communication signals may be above the capture threshold of the heart, but may be delivered during a refractory period of the heart and/or may be incorporated in or modulated onto a pacing pulse, if desired.

The conducted communication signals may be voltage pulses, current pulses, biphasic voltage pulses, biphasic current pulses, or any other suitable electrical pulse as desired. In some examples, the conducted communication signals may be combinations of voltage pulses and current pulses. Accordingly, in examples where the conducted communication signals include voltage pulses, the devices of system 500 may include appropriate circuitry, such as in a communication module or a pulse generator module, for generating voltage pulses. When generating a voltage pulse, the amplitude of the voltage is controlled, and the amplitude of the current is dependent on the voltage amplitude and the resistance of the transmission medium. In examples where the conducted communication signals include current pulses, the devices of system 500 may include appropriate circuitry for generating current pulses. When generating a current pulse, the amplitude of the current is controlled, and the amplitude of the voltage is dependent on the current amplitude and the resistance of the transmission medium. In examples where the conducted communication signals comprise both voltage and current pulses, the devices of system 500 may include appropriate circuitry for generating both voltage pulses and current pulses. Some example features of conducted communication signals that the devices of system 500 may use are described with respect to FIG. 6.

The conducted communication signals may be modulated in any suitable manner to encode communicated information. For example, and in some cases, the conducted communication signals may be pulse width modulated. Alternatively, or additionally, the time between successive conducted communication signals may be modulated to encode desired information. Illustrative techniques for encoding information with conducted communication signals and sending messages between devices are described with respect to FIGS. 10-15.

FIGS. 6A-6D illustrate some example features of conducted communication signals that devices of system 500 may use when communicating. Although the examples are described with respect to conducted voltage signals, it is contemplated that the devices of system 500 may use conducted current signals.

Figure 6A:
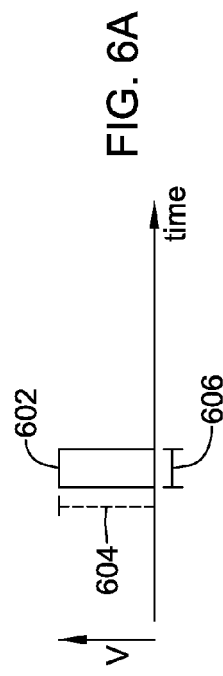
FIGS. 6A-D are schematic diagrams illustrating communication pulses, in accordance with an example of the present disclosure.

FIG. 6A depicts an example communication voltage pulse that devices of system 500 may use in a conducted communication scheme. Specifically, FIG. 6A depicts communication voltage pulse 602, which has a voltage amplitude 604 and pulse width 606. Communication voltage pulse 602 is a monophasic, positive polarity communication voltage pulse. In such examples, amplitude 604 may be three, four, or five volts, or any other suitable amplitude. In some instances, amplitude 604 may be correlated to the voltage of the battery of the device that generates the voltage pulse. For example, amplitude 604 may between one and two times the voltage of the battery of the generating device. If the voltage of the battery of the generating device is six volts, then amplitude 604 may be between six and 12 volts. A voltage multiplier (not shown) may be used to multiply the voltage of the battery for use in generating the communication pulses. Pulse width 606 may be one, five, ten, fifteen, twenty microseconds, or any other suitable length of time.

Figure 6B:
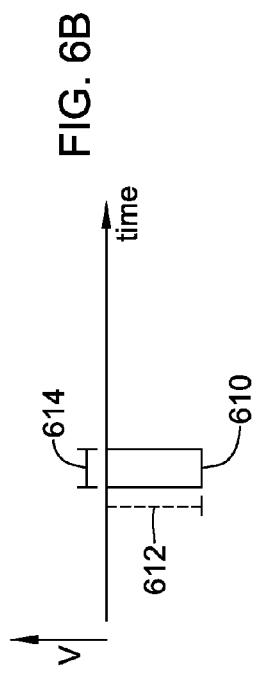

FIG. 6B depicts another example communication voltage pulse that devices of system 500 may use in a conducted communication scheme. FIG. 6B depicts communication voltage pulse 610, which has a voltage amplitude 612 and pulse width 614. In contrast with communication voltage pulse 602, communication voltage pulse 610 is a monophasic, negative polarity communication voltage pulse. That is, amplitude 612 is negative. For instance, amplitude 612 may be negative three, negative four, or negative five volts, or any other suitable amplitude. Pulse width 614 may be one, five, ten, fifteen, twenty microseconds, or any other suitable length of time. As with amplitude 604, in some examples, amplitude 612 may be correlated to a battery voltage of the device that generates the voltage pulse.

Figure 6C:
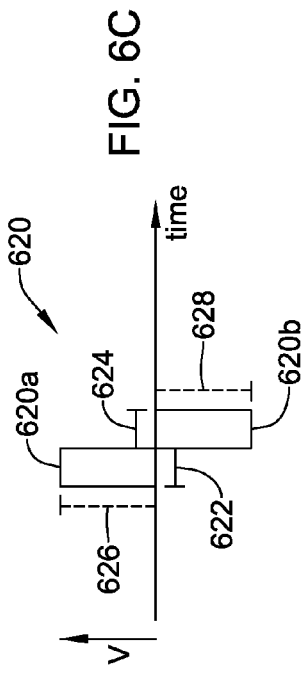
Figure 6D:
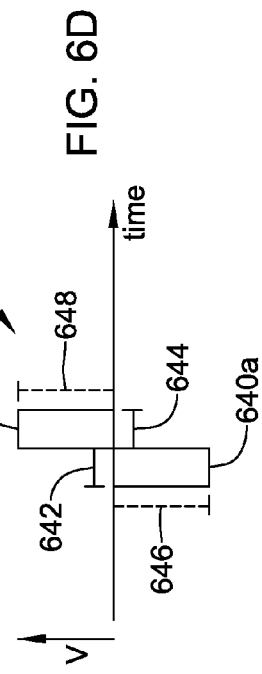

FIGS. 6C and 6D both depict other examples of communication voltage pulses that devices of system 500 may use in a conducted communication scheme. FIG. 6C depicts communication voltage pulse 620, which is a biphasic communication voltage pulse beginning with positive portion 620a and ending with negative portion 620b. Each of positive portion 620a and negative portion 620b have individual amplitudes and pulse widths. Amplitudes 626 and 628 may have a magnitude of three, four, or five volts, or any other suitable amplitude, with amplitude 626 having a positive value and amplitude 628 having a negative value. Additionally, in some examples, amplitudes 626 and 628 may be correlated to a battery voltage of the device that generates the voltage pulse. Pulse widths 622 and 624 may each be one, five, ten, fifteen, twenty microseconds, or any other suitable length of time. Accordingly, some example total pulse widths of communication voltage pulse 620 may be two, ten, twenty, thirty, forty microseconds, or any other suitable length of time. FIG. 6D depicts communication pulse 640, including negative portion 640a, positive portion 640b, pulse widths 642 and 644, and amplitudes 646 and 648. Communication voltage pulse 640 is a biphasic communication voltage pulse similar to communication voltage pulse 620, except that voltage pulse 640 has negative portion 640a preceding positive portion 640b. Pulse widths 642 and 644 and amplitudes 646 and 648 may have similar values to those described for communication voltage pulse 620, or different values.

In some examples, the communication voltage pulses depicted in FIGS. 6A-6D may have amplitudes and pulse widths that vary, either between pulses or between a positive and negative portion of a pulse. For instance, where a device generates multiple monophasic communication voltage pulses, the first communication voltage pulse may have a first set of characteristics, in terms of amplitude and pulse width, and a second communication voltage pulse may have a second set of characteristics, where at least some of the second set of characteristics differs from the first set of characteristics. In some instances, the polarity between successive monophasic communication voltage pulses may also vary. Although not shown, in some examples there may be a delay between biphasic pulses. For example, in FIGS. 6C and 6D there may be a delay between pulses 620a and 620b or 640a and 640b respectively. The delay may be one, two, five, ten microseconds, or any other suitable length of time.

In examples where a medical device generates biphasic communication voltage pulses, the amplitude of the first portion of the communication voltage pulse may differ from the second portion of the communication voltage pulse. Additionally, the pulse width of the first portion of the communication voltage pulse may be different than the second portion of the communication voltage pulse. Though, the characteristics, in terms of amplitude and pulse width, and even polarity, may differ between successive biphasic communication voltage pulses instead of or in addition to differing between different portions of the same biphasic communication voltage pulse.

As discussed above, devices of system 500 may generate communication voltage pulses that are sub-threshold voltage pulses—voltage pulses which do not capture the heart. This may allow the devices of system 500 to communicate over a broad range of the cardiac cycle without interfering with any delivery of electrical stimulation therapy, for example by causing undesirable capture of the heart. Accordingly, the conducted communication voltage pulses used by the devices of system 500 may generally have characteristics that fall within a safe region 710, as depicted in FIG. 7.

Figure 7:
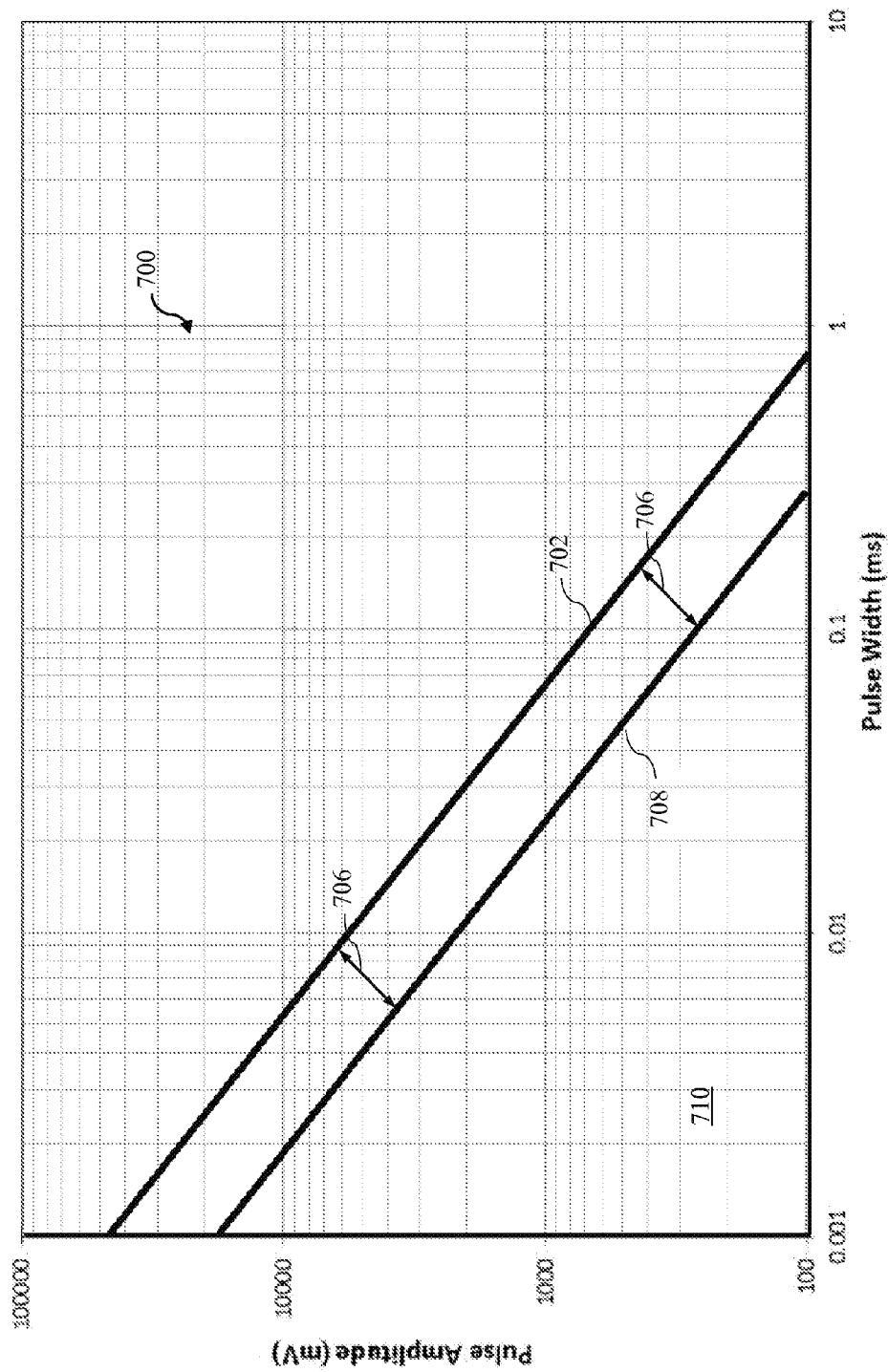
FIG. 7 shows an illustrative graph of pulse amplitude vs. pulse width, in accordance with aspects of the present disclosure.

FIG. 7 shows graph 700, which is a graph of pulse amplitude vs. pulse width, in millivolts and milliseconds. Curve 702 represents the combinations of pulse amplitudes and pulse widths of a voltage pulse that, when delivered to tissues of a patient, result in capture of the patient's heart. In this Figure, any combinations of pulse amplitude and pulse width that lie on curve 702, or above and to the right of curve 702, have been determined to capture a heart in animal test models. Any combinations of pulse amplitude and pulse width that lies below and to the left of curve 702 were determined to not result in capture of the heart. This region is defined as safe zone 710.

In human patients, curve 702 may vary by patient, and is somewhat a function of time and/or other factors. Accordingly, the exact combinations or pulse amplitudes and pulse widths that result in capture and do not result in capture may vary, resulting in some unpredictability with respect to whether a given combination of pulse amplitude and pulse width will capture the heart. In some examples, then, safe region 710 may be the combinations of pulse amplitudes and pulse widths that lie below and to the left of a second curve, curve 708. Second curve 708 may be of a similar shape as curve 702, only shifted down and to the left by a safety margin 706. Safety margin 706 may be set such that if curve 702 does change as a function of time or other factors, curve 702 will not, or is statistically unlikely to, drift below and to the left of curve 708. Accordingly, in some examples, safe region 710 may encompass the combinations of pulse amplitudes and pulse widths below and to the left of curve 708, rather than curve 702.

Consequently, the devices of system 500 may be configured to generate communication voltage pulses with characteristics within safe region 710. In some examples, safe region 710 may be predetermined for a particular patient, and the devices of system 500 may be configured to generate communication voltage pulses with a combination of pulse amplitude and pulse width that falls within predetermined safe region 710. In some instances, one or more of the devices of system 500 may be configured to determine safe region 710 by generating a plurality of voltage pulses with different pulse amplitude and pulse width characteristics and determining whether the generated voltage pulses capture the heart. In these examples, the devices of system 500 may be configured to periodically determine one or more combinations of pulse amplitudes and pulse widths which result in capture of the heart. After determining which combinations of characteristics of voltage pulses result in capture, the devices of system 500 may be configured to only generate communication voltage pulses that have lower pulse amplitudes and/or shorter pulse widths than those voltage pulses which resulted in capture. The devices of system 500 may alternatively be configured to generate communication voltage pulses with characteristics that are a predetermined amount less than and/or shorter than the characteristics of those voltage pulses that resulted in capture, as a margin of safety. In some instances, the devices of system 500 may be configured to generate voltage pulses within a composite safe region 710 that is predetermined based on determined safe regions for a population of people.

Figure 8:
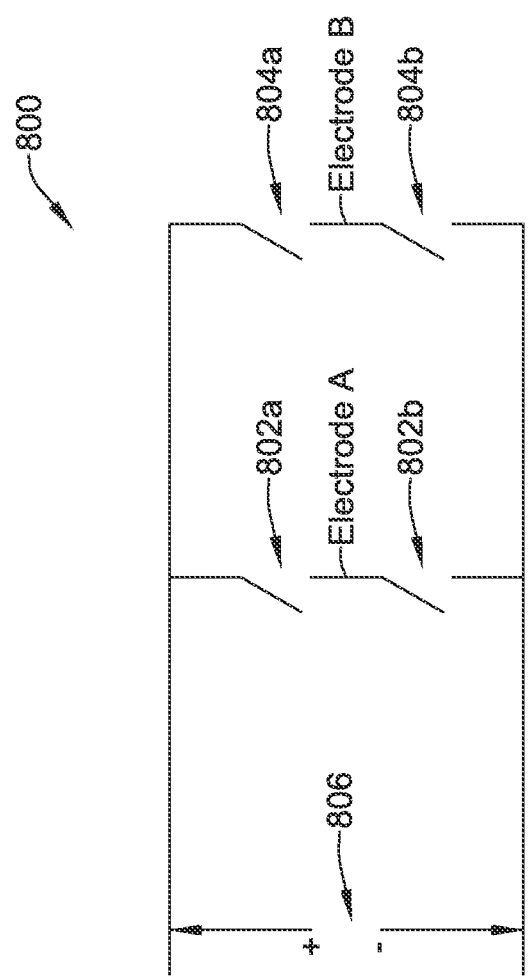
FIG. 8 is a schematic diagram of an example circuit for generating communication pulses, in accordance with one example of the present disclosure.

FIG. 8 is a diagram of an example circuit 800 that a device of system 500 may use to generate communication voltage pulses. In the example shown, circuit 800 may be a part of a communication module. Or, in examples where a pulse generator module generates communication voltage pulses, circuit 800 may be a part of a pulse generator module. Circuit 800 may include double switches 802a and 802b connected to a first electrode and double switches 804a and 804b connected to a second electrode. The illustrative circuit 800 additionally includes voltage source 806. The device using circuit 800 may operate switches 802a, 802b and 804a, 804b in a manner that produces one or more of the communication voltage pulses described herein. For example, the device may close switches 802a and 804b, and open switches 802b and 804a, to produce a positive amplitude communication pulse between Electrode-A and Electrode-B. Conversely, the device may close switches 802b and 804a, and open switches 802a and 804b, to produce a negative amplitude communication pulse between Electrode-A and Electrode-B. To produce a biphasic communications pulse, the device may close switches 802a and 804b, and open switches 802b and 804a, to produce a positive amplitude communication pulse between Electrode-A and Electrode-B, and then immediately, or after a predetermined delay, close switches 802b and 804a, and open switches 802a and 804b, to produce a negative amplitude communication pulse between Electrode-A and Electrode-B. The time that the switches remain in the closed state will determine the corresponding pulse width. In general, the device may operate the switches 802a, 802b, 804a, and 804b in any manner to produce a variety of different communication voltage pulses, such as those described with respect to FIGS. 6A-6D.

Figure 9:
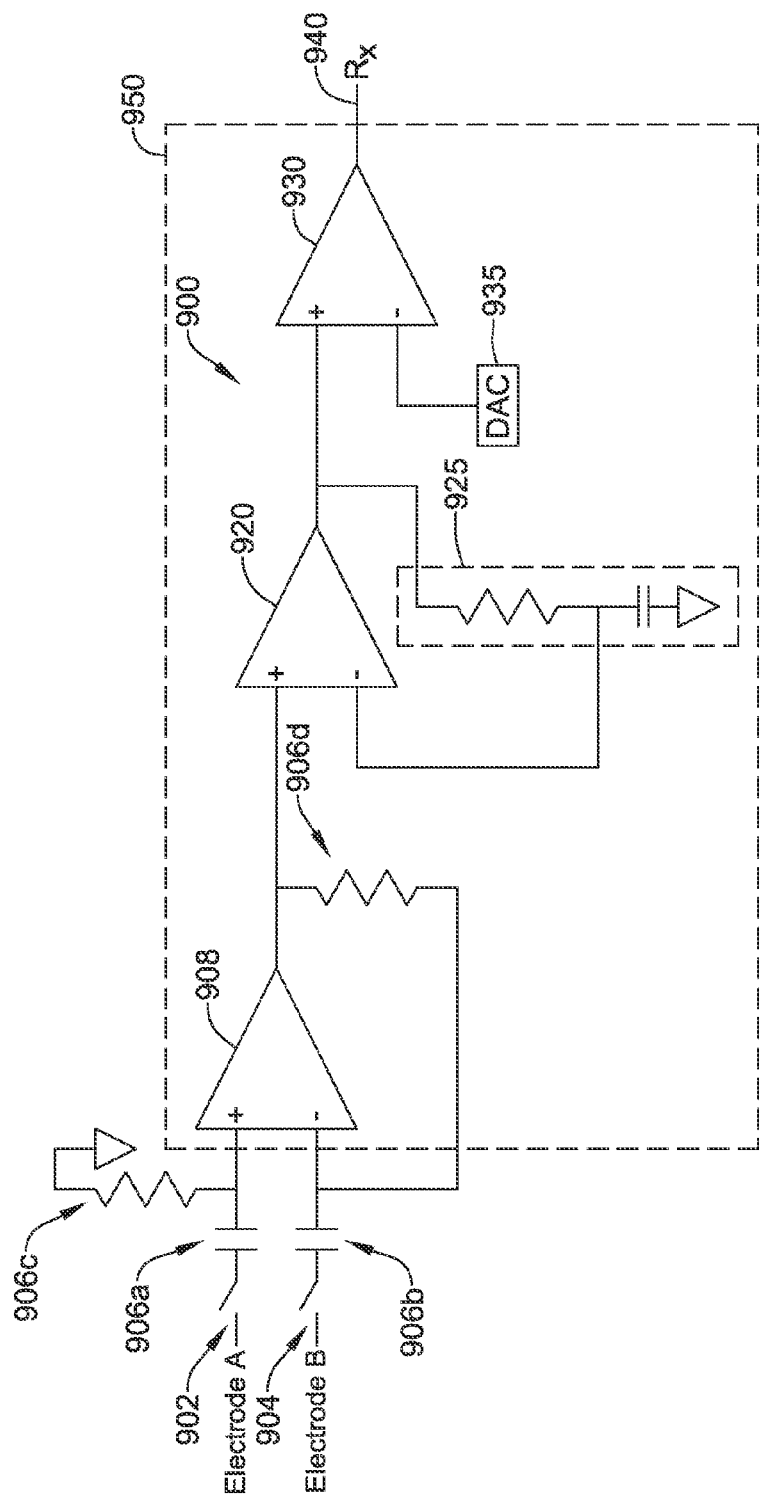
FIG. 9 is a schematic diagram of an example circuit for receiving communication pulses, in accordance with one example of the present disclosure.

FIG. 9 is a schematic diagram of an illustrative circuit 900 that a device of system 500 may be used to sense for communication voltage pulses. For instance, circuit 900 may be included in a communication module of a device. Illustrative circuit 900 depicts two inputs connected to positive and negative terminals of operational amplifier 908. The inputs, for example a first and second electrode, are connected to switches 902 and 904, respectively. The switches 902 and 904 are typically switched together, and may be used to control when the circuit 900 senses for communication pulses. For example, the switches 902 and 904 may be opened when a pacing pulse is expected to be delivered, when a shock is expected to be delivered, when an intrinsic heartbeat is expected to occur, and/or at other times.

The first input of the circuit 900 may be coupled to a positive input of operational amplifier 908 through one or more circuit elements. In at least one example, the circuit elements may include a capacitor 906a and resistor 906c. In such examples, capacitor 906a and resistor 906c may operate as a high-pass filter before the signal is fed into the positive terminal of amplifier 908, thereby attenuating low frequency signals. In a similar fashion, the second input may be coupled to the negative input of operational amplifier 908 through one or more circuit elements. In the example of FIG. 9, the second input is coupled to the negative input of operational amplifier 908 by capacitor 906b and resistor 906d. Capacitor 906b and resistor 906d may function to operate as a high-pass filter before the signal is fed into the negative terminal of operational amplifier 908, thereby attenuating low frequency signals.

Receiver circuit 950, which includes operational amplifier 908, may receive the signals from two electrodes as described above. As the signal passes through receiver circuit 950, the various elements may cooperate to amplify and/or filter the differential signal to reduce noise and/or enhance features of any communication voltage pulses present in the signal. The signal may then exit receiver circuit 950 as an amplified and/or filtered signal at 940. The amplified and/or filtered signal may then be fed into a processor or other circuit which may detect one or more communication voltage pulses.

Receiver circuit 950 may contain one or more amplifiers and/or filtering elements. For example, receiver circuit 950 may contain amplifiers 920 and 930. More specifically, the output of amplifier 908 may be fed into the positive terminal of amplifier 920. The output of amplifier 920 may be modified by one or more circuit elements 925 before being fed-back to the negative terminal of amplifier 920. The output of amplifier 920 may also be fed into the positive terminal of amplifier 930, and a signal from a digital-to-analog converter may be fed into the negative terminal of amplifier 930. The output of amplifier 930, then, may be the amplified and/or filtered signal that is output of receiver circuit 950 at 940.

In at least some examples, the devices of system 500 may be constantly receiving and processing signals. For instance, switches 902 and 904 may be constantly closed, conducting sensed signals into circuit 900. In other examples, the devices of system 500 may be receiving and processing signals at least a majority of the time (e.g. for a majority of each cardiac cycle). Accordingly, circuit 900 may be designed to be low power in order improve battery life. In some examples, circuit 900 may be designed to have a sensitivity of one millivolt or less with a linear input range of 1-to-100 millivolts, but this is just one example. Circuit 900 may be configured for a source impedance of between 300 and 1500 ohms, but again this is just one example.

Figure 10:
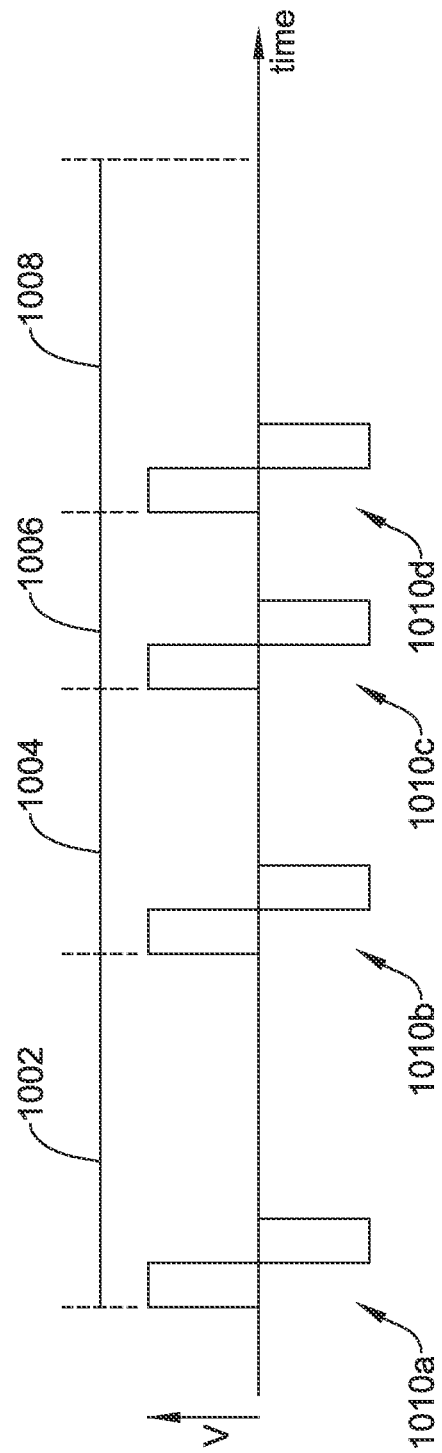
FIG. 10 shows an illustrative timing diagram showing example communication pulses delivered by a medical device in relation to each other, in accordance with an example of the present disclosure.

In some cases, the devices of system 500 may use the elapse time between communication voltage pulses to encode information. FIG. 10 provides some example techniques for encoding information using the elapse time between communication voltage pulses. FIG. 10 shows a graph of four example communication voltage pulses 1010a-1010d. Communication voltage pulses 1010a-1010d are separated by three distinct time periods, 1002, 1004, and 1006, respectively. In the example shown, the last time period 1008 does not separate one communication voltage pulse 1010d from another communication voltage pulse. Rather, time period 1008 is simply a threshold length of time extending from communication voltage pulse 1010d, without a subsequent communication voltage pulse 1010 occurring before the end of the threshold length of time. In some cases, the devices of system 500 may identify communication symbols based on the length of the time between the communication voltage pulses 1010a-1010d. For example, if the time between two communication voltage pulses falls within a first time range, then a first symbol may be identified. If the time between two communication voltage pulses falls within a second time range, then a second symbol may be identified. If the time between two communication voltage pulses falls within a third time range, then a third symbol may be identified, and so on. In one example, a sync symbol is identified when the time between two communication voltage pulses falls within a range of 800-1100 microseconds, a "1" symbol is identified when the time between two communication voltage pulses falls within a range of 550-700 microseconds, and a "0" symbol is identified when the time between two communication voltage pulses falls within a range of 350-450 microseconds. In some cases, the "0" and "1" symbols correspond to "0" and "1" bits, respectively, as the devices of system 500 may operate in a base two number system. These are just some examples. It is contemplated that any number of different symbols may be included in the communication protocol, with different symbols assigned to different times or time ranges. In some case, if a communication voltage pulse is not followed by another communication voltage pulse within a threshold amount of time (e.g. time period 1008), an end or frame (EOF) symbol may be identified. The threshold amount of time (e.g. time period 1008) may be, for example, 1250 microseconds or more.

In some cases, the time between communication voltage pulses may be tracked using an internal clock. It is contemplated that the sending device may include an internal clock that oscillates at a clock frequency. Likewise, the receiving device may include an internal clock that oscillates at the same (or different) clock frequency. When so provided, each symbol to be communicated may be assigned a different number of clock cycles between communication voltage pulses. For example, a synchronization symbol may be assigned 24 clock cycles, which for a clock frequency of 25.6 kHz, would correspond to a delay between communication voltage pulses of about 938 microseconds. A range may be provided to help compensate for noise, temperature changes, voltage variances, clock drift, etc. The range may be, for example, +/−10%, or in the example given above, may be from about 844 microseconds to about 1032 microseconds. A "1" symbol may be assigned to 16 clock cycles, which for a clock frequency of 25.6 kHz, would corresponds to a delay between communication voltage pulses of about 625 microseconds. A range may be provided around this figure to help compensate for noise, temperature changes, voltage variances, clock drift, etc. The range may be, for example, +/−10%, or in the example given above, may be from about 563 microseconds to about 688 microseconds. Likewise, a "0" symbol may be assigned to 10 clock cycles, which for a clock frequency of 25.6 kHz, would correspond to a delay between communication voltage pulses of about 391 microseconds. A range may be provided around this figure to help compensate for noise, temperature changes, voltage variances, clock drift, etc.

To transmit a desired symbol, the sending device may provide a first communication voltage pulse, then count the number of clock cycles that corresponds to the desired symbol (e.g. 16 clock cycles for a "1" symbol), and then provide a second communication pulse. When the receiving device receives the first communication voltage pulse, the receiving device may start counting internal clock cycles. When the second communication pulse is received, the receiving device may stop counting clock cycles. The receiving device may then compare the number of counted internal clock cycles to the number of clock cycles assigned to each symbol. When a match is found, the desired symbol is identified by the receiving device.

In some cases, the accuracy of the internal clocks in the sending device and/or receiving device may degrade over time. Due to this degradation, the devices of system 500 may begin to determine lengths of time differently with respect to absolute lengths of time, and possibly with respect to each other if the clocks of the devices degrade differently with respect to each other. Accordingly, in examples where time periods 1002, 1004, 1006, and 1008 are ranges of times, the devices of system 500 may still correctly interpret symbols even after some level of clock degradation.

In some cases, the devices of system 500 may be configured to reconfigure their internal clocks on a periodic or other basis. For example, a first device may broadcast a beginning calibration signal, an ending calibration signal, and the length of time between the two signals as determined by the broadcasting device. Each other device may then calibrate their internal clocks so that the time period between the two calibration signals is equal to the length of time sent by the broadcasting device. Such a reconfiguration may help ensure that a clock of a device does not drift too far relative to that of other devices of the system such that the device becomes functionally inoperative.

Whatever the exact lengths of time periods 1002, 1004, 1006, and 1008, in some examples, time period 1002 may be longer than either of time periods 1004 and 1006. In such examples, this arrangement may prevent accidental transmission of one or more symbols from one device to another device, or a device interpreting noise as communication of one or more symbols. For instance, the devices of system 500 may transmit communication voltage pulses to communicate a synchronization symbol before transmitting one or more other symbols, and receiving devices may ignore any other symbols received before receiving a synchronization symbol. In some situations, a receiving device may receive a first, true communication voltage pulse but then receive noise after a length of time shorter than time period 1002. If the noise is similar in morphology to a communication voltage pulse, the receiving device may interpret the noise as a communication voltage pulse. However, since the noise occurred after a shorter length of time than time period 1002, even if the noise occurred at a length of time indicating a "0" symbol or a "1" symbol, the receiving device would ignore those symbols as the receiving device had not yet received a synchronization symbol. In this manner, the devices of system 500 may suppress erroneously transmitted or falsely interpreted symbols.

In some instances, a blanking period may be applied by the receiving device immediately following receiving each communication voltage pulses. During the blanking period, the receiving device may ignore any received communication signals. This may help further reduce noise that might arise immediately after a communication voltage pulse from being interpreted as a valid communication voltage pulse. The blanking period may be anywhere between one-quarter to three-quarters the length of time period 1002, or any other suitable length of time. In one example, the blanking period may be, for example about 250 microseconds. In some cases, the sending device may apply a similar blanking period, during and/or following the transmission of a communication voltage pulse. Such a blanking period may help prevent the circuitry of the sending device, which senses for conducted communication signals from other devices, from sensing the communication voltage pulses generated by the sending device.

In FIG. 10, the receiving device(s) of system 500 may identify the elapse time 1002 between communication voltage pulses 1010*a* and 1010*b*, and interpret that elapse time 1002 as, for example, a synchronization symbol. Likewise, the receiving device(s) of system 500 may identify the elapse time 1004 between communication voltage pulses 1010*b* and 1010*c*, and interpret that elapse time 1004 as, for example, a "1" symbol. Moreover, the receiving device(s) of system 500 may identify the elapse time 1006 between communication voltage pulses 1010*c* and 1010*d*, and interpret that elapse time 1006 as, for example, a "0" symbol. In some cases, the receiving device(s) of system 500 may detect that communication voltage pulse 1010*d* is not followed by another communication voltage pulses within the threshold amount of time 1008, and may interpret that as an End of Frame (EOF) symbol. This particular example is only illustrative, and it is contemplated that different symbols, different time delays and different sequences may be used, depending on the application.

In some examples, the devices of system 500 are continuously (although possibly punctuated by blanking periods) listening for conducted communication signals. That is, the devices of system 500 may not send out wake-up signals or establish specific communication connections before sending out conducted communication signals to other devices. Instead, the devices of system 500 may rely on synchronization pulses as a signal to the other devices of system 500 that the sending device is sending a message. In some cases, an EOF symbol may be a signal that the sending device has communicated the entire message.

In the example of FIG. 10, time periods 1002, 1004, 1006, and 1008 are depicted as being measured from a leading edge of each communication voltage pulse 1010. However, in other examples, time periods 1002, 1004, 1006, and 1008 may be measured off of other features of communication voltage pulses 1010. For instance, the devices of system 500 may measure time periods 1002, 1004, 1006, and 1008 from the trailing edge of communication voltage pulses 1010. In still other examples, the devices of system 500 may measure time periods 1002, 1004, 1006, and 1008 from the inflection point of communication voltage pulses 1010. Additionally, the devices of system 500 may not begin measuring a time period from a feature of communication voltage pulses 1010, for example the leading edge, until the amplitude of the communication voltage pulse reaches a threshold level. In some cases, the devices of system 500 may measure time periods 1002, 1004, 1006, and 1008 from a zero-crossing point of communication voltage pulses 1010. These are just some examples.

Figure 11:
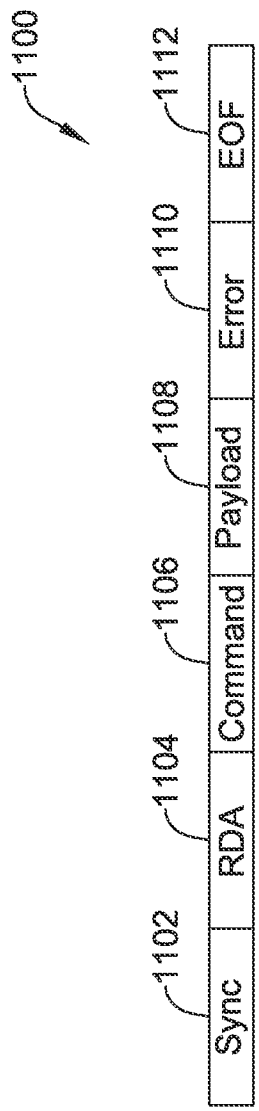
FIG. 11 shows an illustrative command message structure, in accordance with an example of the present disclosure.

FIG. 11 illustrates an example message 1100 that the devices of system 500 may use to communicate data, commands and/or other information. The illustrative message 1100 may be a command message that includes a command for causing another device to take an action. Message 1100 may include a synchronization field 1102, an address field 1104, a command field 1106, a payload field 1108, an error check field 1110, and an EOF field 1112. Synchronization field 1102 of message 1100 may include one or more synchronization symbols. As discussed previously, a synchronization symbol may indicate to receiving devices that a message is being initiated.

Address field 1104 may include symbols that represent a relative device address (RDA). Each device of the system 500 may have an RDA that uniquely identifies the device in the system 500. In some examples, the RDA may include three bits, allowing for eight devices with unique RDAs. In other examples, however, the address field 1104 may have greater or fewer RDA bits, as desired.

Address field 1104 may identify the devices to which the message is directed. As described previously, in some examples, the devices of system 500 may be constantly listening for conducted communication signals. Accordingly, each communication voltage pulse sent by a sending device may be received by all devices of the system 500. However, once a device has received a synchronization symbol and an RDA, the device may attempt to match its own RDA (stored in local memory) with the received RDA. If the device determines that its RDA does not match the received RDA, the device may ignore the rest of the message. In some examples, this may simply mean that the device may not take action based on the command field 1106 in the message. In other examples, the device may begin a blanking period or otherwise disable its circuitry that senses for conducted communication signals. If a device determines that the received RDA matches its own RDA, the device may continue to process the message, e.g. take action according to a received command. In this manner, the devices of system 500 may direct messages to specific devices in the system. As used herein, the term 'receiving device' may indicate any device that senses the conducted communication signals, e.g. all devices of the system within range of the conducted communication signals. This disclosure uses the term 'intended device' to indicate the device to which a sending device directs a message.

In some examples, the devices of the system 500 may have multiple associated RDAs. It may be desirable in some examples for the devices of system 500 to direct messages to multiple devices. In examples where a device has only a single unique RDA, the sending device would send multiple separate messages each with a different RDA. However, in examples where devices have more than one associated RDA, at least one of the associated RDAs may not be unique. As one example, two separate devices may have their own associated unique RDAs and a second, non-unique RDA which is the same for both devices. Accordingly, to direct a message to both of the devices, a sending device would need only to send a single message with the second RDA, as the second RDA is associated with both the devices. In this manner, a device may generally have one unique RDA and any suitable number of non-unique RDAs which are also associated with one or more other devices to facilitate communication from one device to a number of devices. In at least some examples, each device may have an RDA that is the same across all devices in the system. Accordingly, when a device sends a message with such an RDA, the message is directed to all of the devices in the system 500. Although the devices of system 500 have been described as having RDAs that are three bits in length, other example systems may have RDAs that have more or less bits. The specific length of an RDA may be chosen according to the number of unique devices in a system and the desired combinations of devices for the purpose of directing messages.

In one example message, command field 1106 may include a three bit command. However, in other examples, the command field may be any number of bits. The command field may represent an instruction by the sending device for the receiving device or devices to perform one of a number of predefined commands.

Payload field 1108 may include one or more bits of data that the sending device includes in the message. For some commands, the receiving device may need the data, address and/or other information included in payload field 1108 to take the desired action based on the command received in command field 1106. In some examples, payload field 1108 has a range of possible sizes, such as zero bits to twenty-four bits. However, in other examples, payload field 1108 may be any other suitable size. Alternatively, the payload field may have a fixed length, which in some cases may depend on the command specified in command field 1106. For instance, for a "Read Byte" command, payload field 1108 may be a nine bit address. However, for a "Write Byte" command, payload field 1108 may include a nine bit address and an eight bit data field for a total of seventeen bits.

Error check field 1110 may include an error checking code, which the receiving device may use to determine if the received message was corrupted during transmission. For example, the contents of error field 1110 may include bits that are used by the receiving device in a parity check scheme, a checksum scheme, a cyclic redundancy check scheme, and/or some other type of error checking scheme. Error check field 1110 may also include an error correction scheme. For example, error check field 1110 may include hamming, Reed-Solomon or other correction codes.

In some examples, if the receiving device determines that the message was corrupted, the receiving device may send a command to the sending device to re-send the message. However, in some example systems, there may not be a command to request that the sending device resend the message (as is missing in Table 1). In such examples, if the corrupted message was a command message, the receiving device may take no action and send no response message (described below with respect to FIG. 12). After not receiving a response message within a predetermined period of time, the sending device may resend the command message. If the corrupted message was a response message, the device that sent the command message may simply send the command message again to trigger another response message.

EOF field 1112 may simply be an EOF symbol that the sending device includes to indicate the end of the message. As described above, in some examples, the receiving device may identify an EOF symbol based on a lack of a communication voltage pulse for a threshold period of time (rather than a specific time period between two communication voltage pulses). In such examples, EOF field 1112 may simply represent a lack of a generated communication voltage pulse for a threshold length of time by the sending device, as opposed to sending any affirmative signals or bits.

Table 1 below lists some example commands that a device of system 500 may perform, along with the three bits that identify the command (expressed in hexadecimal in Table 1):

TABLE 1

| Command Type | CMD # | RDA | CMD Payload | Response | Description |
|---|---|---|---|---|---|
| Reset | 0x0 | RDA | None | ACK | Cause a System Reset. |
| ID (pairing) | 0x3 | new RDA | 24-bit Unique device ID [23:0] = serial # | ACK if serial # matches; else none | Assign the RDA in the message to the device if the 24-bit payload matches the serial number. |
| Read Byte | 0x4 | RDA | 9-bit [8:0] = address | Byte if ok, else none | Read a single device byte from the address specified. |
| Write Byte | 0x6 | RDA | 17-bit [16:8] = address [7:0] = data | Ack if ok, else none | Write a single device byte to the address specified. |
| Read Multiple | 0x7 | RDA | 17-bit [16:8] = address [7:0] = count | Multiple Bytes if ok, else none | Read up to 8 consecutive bytes from the device. The first byte in the payload will be the value from the address. The second byte will be from the next consecutive and so on. |
| ACK | 0x1 | RDA | 0-bit | | Acknowledge an ID, PING, or WRITE_BYTE command. |
| PING | 0x1 | RDA | 0-bit | ACK | Used for faster polling of devices. |
| DEBUG | 0x5 | Global | 9-bit [8:0] = address | Byte if ok, else none | This special command may be used for identifying two devices with a global RDA. The turn-around time for this command will be based on the last 6-bits of the device's serial number. The turn-around time will be equal to 20 ms × serial_number[5:0]. |

TABLE 1-continued

| Command Type | CMD # | RDA | CMD Payload | Response | Description |
|---|---|---|---|---|---|
| | | | | | This allows two devices to respond w/o corrupting each other. |
| OPEN | 0x2 | RDA | n/a | n/a | Open slot for a future command. |

The "command type" column lists the names of the various commands that a device may include in the illustrative message 1100 of FIG. 11. The "CMD #" column references a specific three bit code used to uniquely identify each command. In Table 1, the three bit code is expressed in a hexadecimal format. Accordingly, 0x0 may be expressed in binary as 000, 0x1 may be expressed as 001, 0x2 may be expressed as 010, and so on. When an intended receiving device receives the three bit command, that device may match up the received three bits to the commands expressed in Table 1, and may take the requested action based on the identified command. In some systems, more commands may be defined and each command may be identified by a greater number of bits. The "RDA" column identifies the type of RDA that the sending device needs to include in the messages for each command. The "CMD Payload" column identifies the specific data that the sending device needs to include in the message for each command. The "Response" column describes the type of response that the intended receiving device (or devices) will return for each command. Finally, the "Description" column gives a general description of the function of each command. Descriptions of each of the commands listed in Table 1 are described below:

Reset Command

After a device receives a "Reset" command (and has an RDA that matches the RDA specified in the RDA field of the Reset command), the receiving device performs a reset. In one example, the receiving device may temporarily cut power to its processing module and/or memory circuit. This power cycle may cause the memory circuit to lose one or more stored parameters, for example if the memory circuit includes at least one volatile memory portion. In some cases, memory circuit may include at least one non-volatile memory portion. In such examples, the device may retain one or more parameters that are stored in the non-volatile memory portion. While power cycling is one way to perform a reset, it is contemplated that any suitable method may be used to reset the receiving device.

ID (Pairing) Command

After receiving the "ID (pairing)" command, a receiving device may associate itself with a specific RDA. In one example, each receiving device may have a unique identifier stored in a non-volatile memory. As one example used herein, the unique identifier may be a serial number associated with a device, such as at the time of manufacture or thereafter. Before associating itself with any RDA, a device may receive and process all messages as if the device were the intended receiving device. If a message including an ID (pairing) command is received, the receiving device may determine if the serial number specified in the payload field matches its own serial number. If the serial numbers match, the receiving device may associate the RDA specified in the address field of the message with itself, and store the RDA in its local memory (non-volatile or volatile memory). In some examples, this pairing may only be done once for each device for the life of the device, while in other cases, this pairing may be done at any suitable time. In some examples, a device that is not to be a part of a medical device system for delivering electrical stimulation therapy to a patient may issue one or more ID (pairing) commands to the medical devices that are to be part of a medical device system for delivering electrical stimulation therapy to a patient. For example, a programmer device may issue ID (pairing) commands to each medical device of a medical device system to assign RDAs to each of the medical devices. The programmer device may only be used once before or at the time of implantation of the medical devices into a patient or may only be used at limited times, such as in a medical office setting, for retrieving information from the medical devices of the system or changing settings of the medical devices. Accordingly, it may not be the case in some examples that the device sending ID (pairing) commands is also a device that communicates with devices of the medical device system in order to deliver electrical stimulation therapy to the patient.

Read Byte Command

If a receiving device receives a "Read Byte" command (and has an RDA that matches the RDA that is specified in the RDA field of the Read Byte command), the receiving device reads the data byte stored at the address included in the payload field of the message, and sends the requested data byte to the sending device.

Write Byte Command

If a device receives a "Write Byte" command (and has an RDA that matches the RDA that is specified in the RDA field of the Write Byte command), the receiving device may write the data byte specified in the payload field of the message to the address specified in the payload field of the message. In the example shown, nine bits of the payload field may specify a memory address, and eight bits may specify the data to be written. In some examples, the payload field of the message may be structured differently.

Read Multiple Command

If a device receives a "Read Multiple" command (and has an RDA that matches the RDA that is specified in the RDA field of the Read Multiple command), the receiving device may read multiple data bytes from its memory, and send the multiple data bytes to the sending device. In one example, the payload field of the message may specify a starting memory address as well as number of bytes. The receiving device may read data bytes beginning at the specified starting memory address and continuing reading subsequent memory addresses until the specified number of bytes have been read, and then send the requested data bytes to the sending device. In some examples, the receiving device may read from consecutive addresses that increase relative to the specified starting address. In other examples, the receiving device may read from consecutive addresses that decrease relative to the specified starting memory address. In still other examples, the sending device may specify whether the receiving device should read and send data from memory addresses that increase or decrease relative to the specified starting memory address.

ACK and Ping Commands

If a device receives an "ACK" command (and has an RDA that matches the RDA that is specified in the RDA field of the ACK command), the message does not have a payload field, and the receiving device may take no action based on the command. If a receiving device receives a "PING" command (and has an RDA that matches the RDA that is specified in the RDA field of the PING command), the receiving device may simply respond with a message having an "ACK" command. As with the "ACK" command, a message that includes a "PING" command may not have any payload field.

Debug Command

The "DEBUG" command may be sent in a message with an RDA that is shared by at least two devices (e.g. a global RDA such as 111). The DEBUG command may include a payload field that specifies a memory address. Each intended receiving device (based on RDA) may read data stored at the specified memory address and send the data back to the sending device. Each intended receiving device may send the data at different times. In one example, each intended receiving device may wait a different number of milliseconds before sending the data so the intended devices do not send the read data at the same time. In some examples, each device may determine to wait time based on an equation with the last six numbers of the device's serial number as one variable. For example, each device may wait for twenty microseconds multiplied by the last six bits of the device serial number.

Open Command

Finally, there may be an undefined command associated with a unique three bit identifier (e.g. 0x2). In Table 1, the command is labeled "OPEN." Devices may later be programmed such that the OPEN command causes the intended device to take some action. For instance, the OPEN command may be used to assign and/or un-assign non-unique RDAs to a single device to allow for more complex multi-device messaging without affecting associated unique RDAs. This is just one example.

Figure 12:
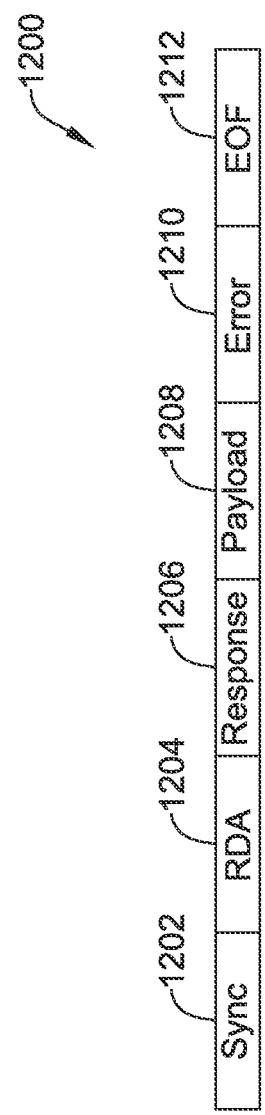
FIG. 12 shows an illustrative response message structure, in accordance with an example of the present disclosure.

Turning now to FIG. 12, FIG. 12 illustrates an example message 1200 that the devices of system 500 may use to communicate data and other information. Message 1200 may be, for example, a response message sent by a receiving device in response to receiving a command message. In the example shown, message 1200 may include a synchronization field 1202, an address field 1204, a response field 1206, a payload field 1208, an error check field 1210, and/or an EOF field 1212. Synchronization field 1202, address field 1204, payload field 1208, error check field 1210, and EOF field 1212 may be similar to synchronization field 1102, address field 1104, payload field 1108, error check field 1110, and EOF field 1112 as described with respect to FIG. 11.

One difference between illustrative message 1200 and illustrative message 1100 is that message 1200 has response field 1206 instead of a command field such as command field 1106. As discussed above, a message with a command field may include a command for an intended receiving device to take some action. A receiving device may send a response message with a response field in response to a command message. Response field 1206 (and sometimes the payload field) may include some sort of explicit response to the received command message. For example, after receiving a message with the ID (pairing) command, and after the intended receiving device matches its serial number to the serial number in the payload field of the received ID (pairing) command message, the intended receiving device may send a response message back to the sending device. In some instances, the response message may include a reference to the ACK command in response field 1206. In some cases, the response message may not include anything in the payload field 1208. However, if the receiving device does not match the received serial number to its own serial number, the receiving device may take no action and send no response message back to the sending device.

If an intended receiving device receives a "Read Byte", "Read Multiple", or "DEBUG" command, the receiving device may read the requested data from one or more memory address. In response to receiving any of the commands, the intended receiving device may send a response message that differs from response message 1200. For example, the response message may include a synchronization field 1202, an address field 1204, a payload field 1208, an error checking field 1210 and/or an EOF field 1212. This response message may lack response field 1206. Payload field 1208 of such response messages may contain the requested data read from the one or more memory addresses. In other examples, the response message may also include response field 1204.

If an intended receiving device receives a "Write Byte", "Reset", or "Ping" command in a command message, the intended receiving device may send a response message back to the sending device with an ACK command in response field 1206. This response message may have no payload field 1208.

Although in the above description, in some examples, the command messages and response messages may omit one or more fields of a message, this may not be true in all cases. For instance, as described above, in a command message having a "PING" command, the command message may not include payload field 1108. However, in other examples, the command message may include a blank payload field. For example, the payload field may include all zeroes. In such messages, the message may be longer. However, each message may be of a constant size (e.g. same number of bits), which may allow for a less complex implementation for processing messages. It additionally may not be the case that payload fields 1108 and 1208 differ based on command types. For instance, payload fields 1108 and 1208 may have a fixed size. The fixed size may be based on a maximum amount of data to be transferred in a single message. In situations where a message does not need the entirety of a payload field for the data to be transmitted, the remainder of the payload field may be blank, for example filled in with zeroes. Again, this may result in messages with constant lengths.

In the above described manner, each field described in FIGS. 11 and 12 may be comprised of a set of communication pulses. For instance, in order to convey information each field may include a plurality of communication pulses in order to convey multiple bits to comprise the conveyed information. However, in some examples, a single communication pulse may be enough to convey information to a receiving device. Accordingly, in some instances, a "set" of communication pulses may include just a single communication pulse, while in other instances a "set" of communication pulses may include multiple communication pulses.

Figure 13:
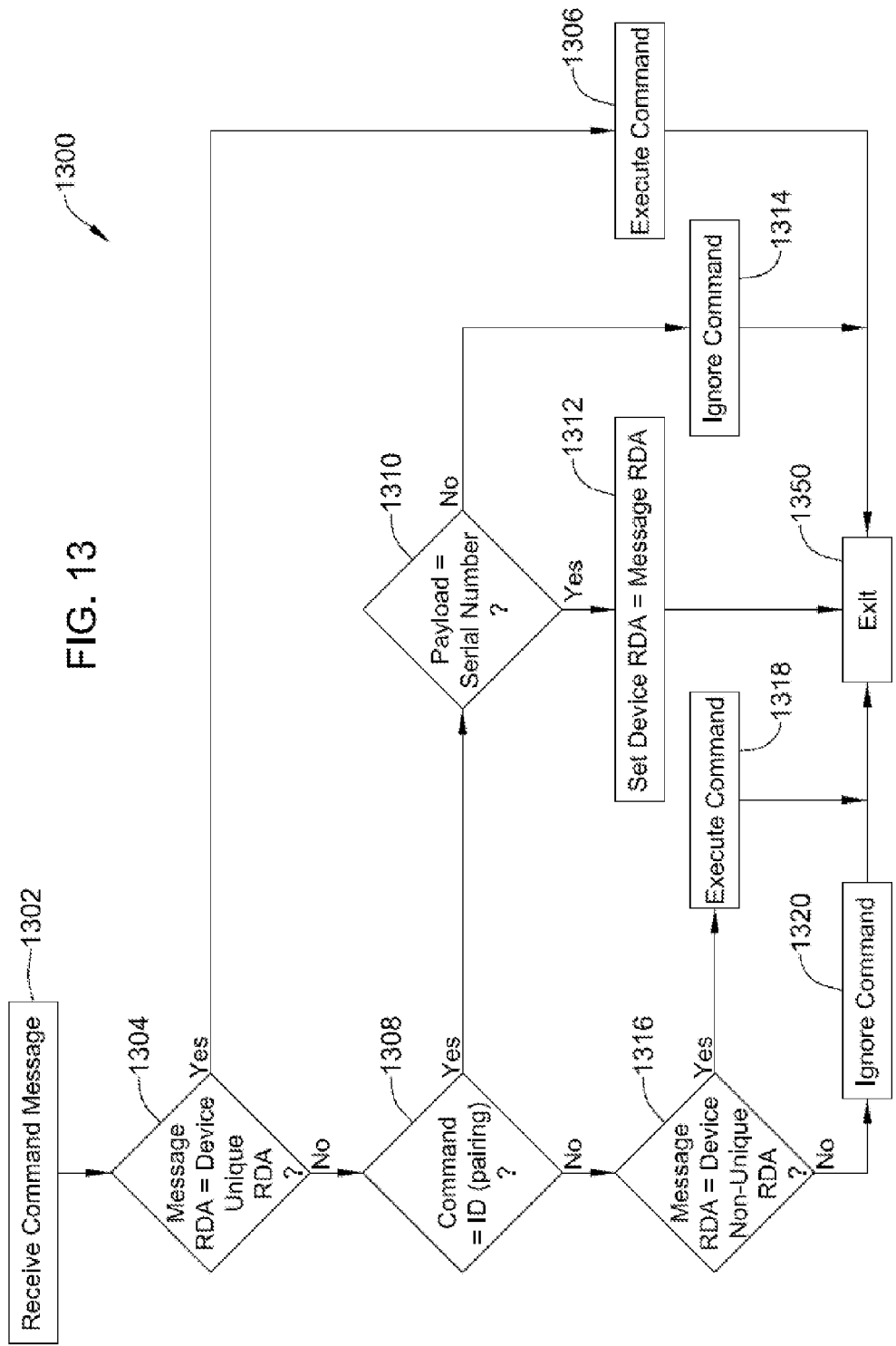
FIG. 13 is a flow diagram of an illustrative method that may be implemented by a medical device or medical device system, such as the illustrative medical devices and medical device systems described with respect to FIGS. 1-4.

FIG. 13 is a flow diagram of an illustrative method 1300 that may be performed by a receiving device. A receiving device may receive a command message, as shown at 1302. The device may determine if the RDA contained in the address field 1104 of the command message matches the unique RDA of the receiving device, as shown at 1304. If the RDA in the command message does match the unique RDA of the receiving device, the receiving device may execute the command reference in the command field 1106 of the command message, as shown at 1306, and then exit as shown at 1350. If the RDA in the command message does not match the unique RDA of the receiving device, for example because the RDA in the command message is different from the unique RDA of the receiving device or the receiving device does not yet have an associated unique RDA, the receiving device may determine if the command in the command field is the ID (pairing) command, as shown at 1308. If the command is the ID (pairing) command, the receiving device may determine if the payload field of the message matches the unique serial number of the receiving device, as shown at 1310. If the payload field does match the unique serial number of the receiving device, the receiving device may set its RDA equal to the RDA in the address field of the message, as shown at 1312. If the payload field does not match the unique serial number of the receiving device, the receiving device may ignore the command, as shown at 1314, and exit as shown at 1350.

If the command is not the ID (pairing) command, the receiving device may determine if the RDA of the command message is one of the receiving device's non-unique RDAs, as shown at 1316. For example, as described previously, each receiving device may have a number of associated non-unique RDAs in addition to each receiving device's unique RDA. If the RDA of the command message is not one of the receiving device's non-unique RDAs, the receiving device may ignore the command, as shown at 1320 and exit as shown at 1350. However, if the RDA of the command message is one of the receiving device's non-unique RDAs, the receiving device may execute the command, as shown at 1318, and exit as shown at 1350.

In some examples, a receiving device may respond differently to command messages based on whether the RDA of the command message is one of the receiving device's non-unique RDAs or the receiving device's unique RDA. For instance, in some instances, a receiving device may perform the functions described above with respect to Table 1 for a given command message if the command message included the receiving device's unique RDA. However, the receiving device may behave differently to one or more of the commands if the RDA of the command message is one of the receiving device's non-unique RDAs. In one example, one of the non-unique RDAs of a receiving device may be a global RDA, e.g. an RDA that is shared by all of the devices of a system. If the receiving device receives a command message with the global RDA, and the command is a Write Byte command or a Reset command, the receiving device may perform those functions but may not send a response message with an ACK response. Additionally, if the command is a Ping, Read Byte, or Read Multiple command, the receiving device may ignore these commands. In other systems, a receiving device may execute the commands in these different ways only if the command message includes one of the receiving device's non-unique RDAs and the receiving devices has not yet set its unique RDA. These are just examples.

In some examples, a device may be preprogrammed with an RDA. For instance, a processing module or memory module may be preprogrammed with a specific RDA so that when the processing module or memory module is incorporated into a device, the device then has an RDA. In other examples, a device may be connected directly to a programming device, and the programming device may set the RDA of the device. In such examples, a device may not include a specific ID command. For example, the device may not recognize and ID command and may not change or set an RDA after receiving an ID command. In such examples, instead of performing a method such as described with respect to FIG. 13, including determining whether a received command is an ID command, the device may simply ignore any message that does not include an RDA that is equal to its own RDA.

Figure 14:
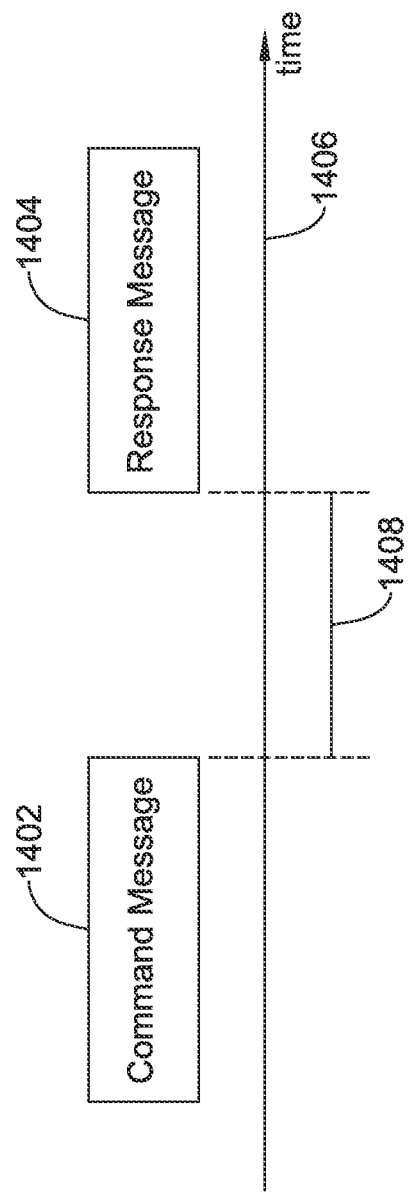
FIG. 14 shows an illustrative timing diagram showing communication of an example command message in relation to communication of an example response message, in accordance with an example of the present disclosure.
Figure 15:
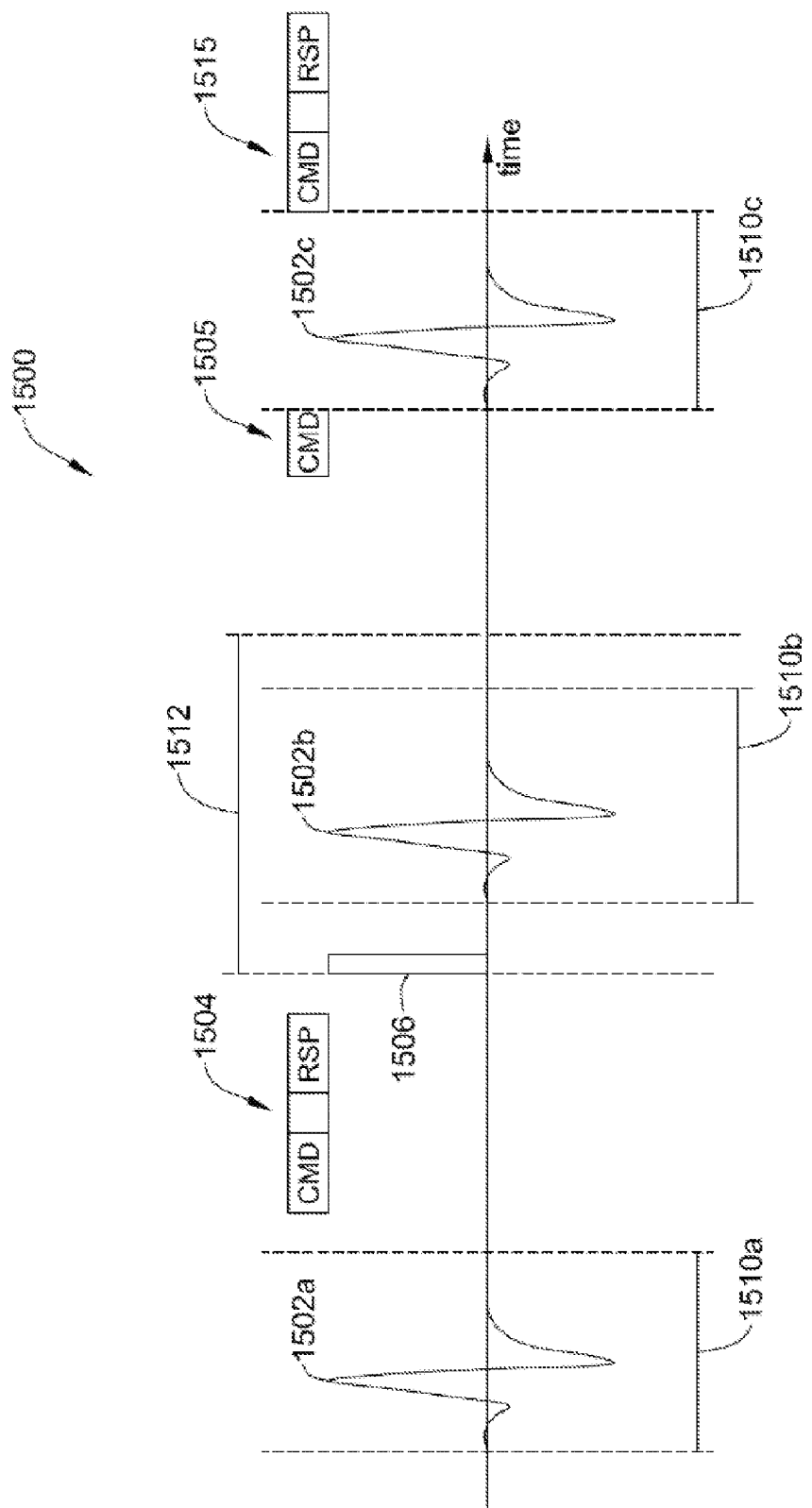
FIG. 15 shows an illustrative timing diagram showing communication of example command message and response message pairs in relation a cardiac cycle, in accordance with an example of the present disclosure.

FIGS. 14 and 15 illustrate various timing schemes of sending command messages and response messages. FIG. 14 displays a command message 1402 and a response message 1404 on a time line 1406. Command message 1402 and response message 1404 are separated by turn-around time 1408. In some examples turn-around time 1408 may be one half of a millisecond. However, in other examples, turn-around time 1408 may be one-quarter, three-quarters, one, or two milliseconds, or any other suitable length of time. In some cases, the turn-around time 1408 may be a fixed or a variable value, which may depend on factors such as, for example, system noise, signal-to-noise ratio, signal strength, processing power of the receiving device, battery level of the receiving device, number of receiving devices in the overall system, etc.

As detailed above with respect to FIGS. 6A-6D, the command message and the response message may each be communication using a plurality of spaced communication pulses each having an amplitude and a pulse width. It is contemplated that the amplitude and/or pulse width of the communication voltage pulses used to send the command message 1402 may be different from the amplitude and/or pulse width of the communication voltage pulses used to send the response message 1404.

More generally, when a first implantable medical device sends a first message (e.g. command message 1402 or response message 1404) from the first implantable medical device to a second implantable medical device, the plurality of spaced communication pulses may have a first amplitude and a first pulse width. When the second implantable medical device sends a second message (e.g. response message 1404 or command message 1402) from the second implantable medical device to the first implantable medical device, the plurality of spaced communication pulses may have a second amplitude and a second pulse width. In some cases, the first amplitude and the second amplitude may be substantially the same (e.g. +/-10%), but the first pulse width and the second pulse width may be substantially different. In some cases, the second pulse width may be 2, 3, 4, 5 or more times the first pulse width. In some cases, the first amplitude and the second amplitude may be substantially different, and the first pulse width and the second pulse width may be substantially the same (e.g. +/-10%). In some cases, the second amplitude may be 2, 3, 4, 5 or more times the first amplitude. In some cases, the first amplitude and the second amplitude may be substantially different, and the first pulse width and the second pulse width may be substantially different.

In some instances, the first implantable medical device may be an implantable subcutaneous cardioverter, and the second implantable medical device may be an implantable leadless cardiac pacemaker. This is just one example. However, because of the different locations of each of these devices in the body, as well as other factors such as battery capacity, the amount of energy that can be provided in the communication pulses without causing capture and/or without causing excessive battery drain, may be substantially different. For these and other reasons, the amplitude and/or pulse width of the communication pulses emitted by each of the devices may be different.

FIG. 15 illustrate various timing schemes for implementing command messages and response messages. An example electrocardiogram 1500 is shown that includes a number of cardiac cycles, shown by QRS waves 1502a-1502c, and command and response message pairs 1504 and 1515. The devices of system 500, in addition to sensing for conducted communication signals as described previously, may also sense for cardiac electrical activity such as intrinsic and/or paced heartbeats. In some examples, intrinsic and/or paced heartbeats may be detected by identifying QRS waves 1502a-1502c of the electrocardiogram 1500. In another example, intrinsic and/or paced heartbeats may be detected by identifying the R wave of the QRS waves 1502a-1502c of the electrocardiogram 1500. Regardless of how the intrinsic and/or paced heartbeats are detected, the devices of system 500 may be configured to begin a message blanking period around detected QRS waves 1502a-1502c, for example message blanking periods 1510a-1510c. The devices of system 500 may be configured to not send any command or response messages during such message blanking periods 1510a-1510c. Said another way, the devices of system 500 may be configured to allow communication between the devices of system 500 except during the blanking periods.

In some cases, the blanking periods 1510a-1510c are initiated after an intrinsic heartbeat is detected, and may extend for a period of time thereafter. For example, blanking periods 1510a-1510c may be initiated after detecting a P wave of a heartbeat signal. In other examples, the blanking periods 1510a-1510c may not begin until after the S wave of the QRS waves 1502a-1502c are detected. In still other examples, the blanking periods 1510a-1510c may begin when the corresponding R wave of the QRS waves 1502a-1502c is detected.

In some examples, a device may detect heartbeat (e.g. a QRS wave) while in the process of sending a message, as illustrated with QRS wave 1502c overlapping command message 1505 of a command and response message pair. In such examples, the sending device may cease sending the message upon detection of QRS wave 1502c and initiation of blanking period 1510c, as indicated in FIG. 15. Although in other examples, the sending device may continue sending the message. In any of these examples, it is possible that the message may not be properly received, either because the message was cut short or because the signal-to-noise ratio of the transmission may be low due to the "noise" caused by the QRS wave 1502c. Once blanking period 1510c has passed, the device may send the command message a second time, as indicated by command and response message pair 1515. In a similar manner, if a device sending a response message detects a heartbeat during the communication of the response message, the device may resend the response message a second time after then end of a blanking period. Although in other examples, the sending device may instead cease sending the response message and not resend the response message after the end of a blanking period. Accordingly, the device that sent the command message may not receive within a predetermined amount of time. In such examples, the device that sent the command message may resend the command message a second time which would prompt a another response message from the receiving device, as described previously with respect to FIGS. 11 and 12 and table 1.

Devices of system 500 may additionally detect stimulation pulses, represented illustratively by stimulation pulse 1506. In such examples, the devices may be configured to implement a blanking period after detecting a stimulation pulse 1506, such as blanking period 1512. In at least some examples, blanking period 1512 may be longer than any of blanking periods 1510a-c, as shown in FIG. 15. However, in other examples, even if blanking period 1512 is longer than any of blanking periods 1510a-c, blanking period 1512 may end at a similar time after paced beat 1502b as blanking periods 1510a and 1510b end after intrinsic beats 1502a and 1502c. The devices of system 500 may deal with detecting stimulation pulse 1506 during transmission of a message in a similar manner to detecting QRS waves 1502a-15102c during message transmission. For example, the devices may be configured to re-send any message or portion of a message pair after the end of blanking period 1512 that overlaps in time with a stimulation pulse 1506. Again, in some examples, the devices may continue sending the message even after detection of a stimulation pulse 1506, but in other examples the devices may cease sending the message upon detection of a stimulation pulse 1506.

In examples where a device begins blanking period 1512, the device may not also institute a blanking period in response to detecting a QRS wave, such as blanking period 1510b. However, in other examples, the device may also institute blanking period 1510b in addition to blanking period 1512. In such examples, the device may not send or re-send any messages until both blanking periods 1512 and 1510b have ended.

Figure 16:
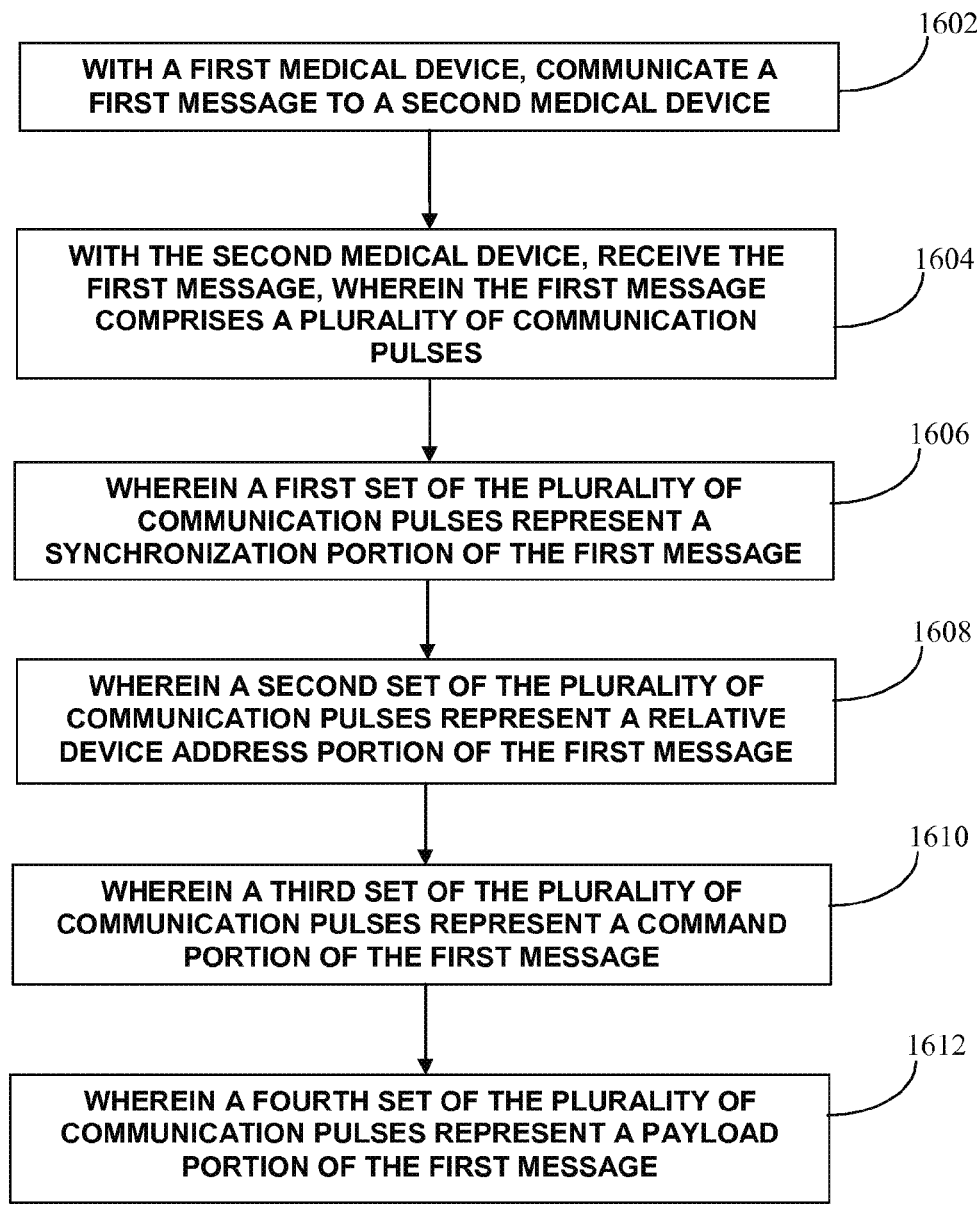
FIG. 16 is a flow diagram of an illustrative method that may be implemented by a medical device or medical device system, such as the illustrative medical devices and medical device systems described with respect to FIGS. 1-5.

FIG. 16 is a flow diagram of an illustrative method that may be implemented by an implantable medical device, such as shown in FIGS. 1-4, or a medical device system such as shown in FIG. 5. Although the method of FIG. 16 will be described with respect to LCP 100 and MD 300, the illustrative method of FIG. 16 may be performed using any suitable medical device or medical device system.

According to the method depicted in FIG. 16, a first medical device, such as MD 300, may be implanted within a patient, such as if MD 300 is an ICP, an ICD, an S-ICD, or may be disposed in proximity to the patient, such as if MD 300 is an external medical device. MD 300 may be part of a medical device system along with a second medical device, such as LCP 100. In such a medical device system, a first medical device, for example MD 300, may communicate a first message to a second medical device, such as LCP 100, as shown at 1602. However, of course, the first medical device may be LCP 100 and the second medical device may be MD 300. In any case, the second medical device may receive the first message, wherein the first message comprises a plurality of communication pulses, as shown at 1604. In some examples, a first set of the plurality of communication pulses may represent a synchronization portion of the first message, as shown at 1606. Additionally, a second set of the plurality of communication pulses may represent a relative device address portion of the first message, as shown at 1608. Further, a third set of the plurality of communication pulses may represent a command portion of the first message, as shown at 1610. Even further, a fourth set of the plurality of communication pulses may represent a payload portion of the first message, as shown at 1612.

Those skilled in the art will recognize that the present disclosure may be manifested in a variety of forms other than the specific examples described and contemplated herein. For instance, as described herein, various examples include one or more modules described as performing various functions. However, other examples may include additional modules that split the described functions up over more modules than that described herein. Additionally, other examples may consolidate the described functions into fewer modules. Accordingly, departure in form and detail may be made without departing from the scope and spirit of the present disclosure as described in the appended claims.

What is claimed:

1. A method for communicating between a plurality of medical devices in a medical device system, the method comprising:
   with a first medical device, communicating a first message to a second medical device;
   with the second medical device, receiving the first message, wherein the first message comprises a plurality of communication pulses, wherein:
      a first set of the plurality of communication pulses represent a synchronization portion of the first message;
      a second set of the plurality of communication pulses represent a relative device address portion of the first message;
      a third set of the plurality of communication pulses represent a command portion of the first message;
      a fourth set of the plurality of communication pulses represent a payload portion of the first message;
   with the second medical device, communicating a second message to the first medical device;
   with the first medical device, receiving the second message, wherein the second message comprises a plurality of communication pulses; and
   wherein each of the plurality of communication pulses of the first message have a first pulse energy, and each of the plurality of communication pulses of the second message have a second pulse energy, wherein the first pulse energy is different from the second pulse energy.

2. The method of claim 1, wherein the synchronization portion of the first message indicates a beginning of the first message.

3. The method of claim 2, wherein the relative device address portion of the first message, the command portion of the first message and the payload portion of the first message follow the synchronization portion of the first message.

4. The method of claim 2, wherein the relative device address portion of the first message precedes the command portion of the first message.

5. The method of claim 1, wherein the relative device address portion of the first message contains a relative device address.

6. The method of claim 5, wherein the relative device address corresponds to either a single device of the medical device system or all of the devices of the medical device system.

7. The method of claim 1, wherein the command portion of the first message contains a command, wherein the command is one of:
   a read command for reading data;
   a write command for writing data;
   a pairing command for pairing the first medical device and the second medical device; and
   a ping command.

8. The method of claim 1, wherein the payload portion of the command comprises data and/or an address.

9. The method of claim 1, wherein a fifth set of the plurality of communication pulses represent an error check portion of the first message.

10. The method of claim 9, wherein the error check portion of the first message contains a cyclic redundancy check code.

11. The method of claim 1, wherein the plurality of communication pulses are sub-threshold communication pulses that are below a capture threshold of the heart.

12. The method of claim 1, wherein the difference between the first pulse energy and the second pulse energy is due to at least one of a difference in pulse width and a difference in pulse amplitude.

13. The method of claim 1, wherein the second pulse energy is greater than the first pulse energy.

14. The method of claim 13, wherein the second pulse energy is at least 5 times greater than the first pulse energy.

15. The method of claim 1, wherein the first message is communicated through body tissue via conducted communication.

16. A medical system comprising:
    a first implantable medical device;
    a second implantable medical device;
    wherein the first implantable medical device is configured to send a first message from the first implantable medical device to the second implantable medical device, wherein the first message comprises a plurality of spaced communication pulses each having a first pulse width;
    wherein the second implantable medical device is configured to send a second message from the second implantable medical device to the first implantable medical device, wherein the second message comprises a plurality of spaced communication pulses each having a second pulse width, wherein the second pulse width is at least two times longer than the first pulse width.

17. The medical system of claim 16, wherein the first implantable medical device comprises an implantable subcutaneous cardioverter, and the second implantable medical device comprises an implantable leadless cardiac pacemaker.

* * * * *